(12) United States Patent
Tricaud et al.

(10) Patent No.: US 10,758,548 B2
(45) Date of Patent: Sep. 1, 2020

(54) METHODS AND PHARMACEUTICAL COMPOSITIONS FOR TREATING PERIPHERAL DEMYELINATING DISEASES

(71) Applicants: INSERM (INSTITUT NATIONAL DE LA RECHERCHE MEDICALE), Paris (FR); UNIVERSITE DE MONTPELLIER, Montpellier (FR)

(72) Inventors: Nicolas Tricaud, Montpellier (FR); Sergio Gonzalez, Montpellier (FR)

(73) Assignees: INSERM (INSTITUT NATIONAL DE LA SANTE ET DE LA RECHERCHE MEDICALE), Paris (FR); UNIVERSITE DE MONTPELLIER, Montpellier (FR)

( * ) Notice: Subject to any disclaimer, the term of this patent is extended or adjusted under 35 U.S.C. 154(b) by 407 days.

(21) Appl. No.: 15/572,001

(22) PCT Filed: May 19, 2016

(86) PCT No.: PCT/EP2016/061334
§ 371 (c)(1),
(2) Date: Nov. 6, 2017

(87) PCT Pub. No.: WO2016/184988
PCT Pub. Date: Nov. 24, 2016

(65) Prior Publication Data
US 2018/0140617 A1    May 24, 2018

(30) Foreign Application Priority Data

May 20, 2015  (EP) .................................... 15305756

(51) Int. Cl.
*A61K 31/575* (2006.01)
*A61P 25/02* (2006.01)
*A61K 31/713* (2006.01)
*G01N 33/50* (2006.01)

(52) U.S. Cl.
CPC .......... *A61K 31/575* (2013.01); *A61K 31/713* (2013.01); *A61P 25/02* (2018.01); *G01N 33/5008* (2013.01)

(58) Field of Classification Search
CPC ..... A61K 31/575; A61K 31/713; A61P 25/02; G01N 33/5008
USPC ........................................................ 514/171
See application file for complete search history.

(56) References Cited

U.S. PATENT DOCUMENTS

2006/0217358 A1* 9/2006 Bordet ................ A61K 31/575
514/177

OTHER PUBLICATIONS

Lenglet T et al: "A phase II-III trial of olesoxime in subjects with amyotrophic lateral sclerosis", European Journal of Neurology, vol. 21, pp. 529-536, Mar. 2014.
Lacomblez Lucette et al: "Dose-ranging study of riluzole in amyotrophic later sclerosis", Lancet (North American Edition), vol. 347, pp. 1425-1431, 1996.

* cited by examiner

*Primary Examiner* — Yevgeny Valenrod
(74) *Attorney, Agent, or Firm* — W&C IP

(57) ABSTRACT

The present invention relates to methods and pharmaceutical compositions for treating peripheral demyelinating diseases. In particular the present invention relates to a method of treating a peripheral demyelinating disease in a subject in need thereof comprising administering to the subject a therapeutically effective amount of an inhibitor of VDAC1 activity or expression.

Figure 1A:
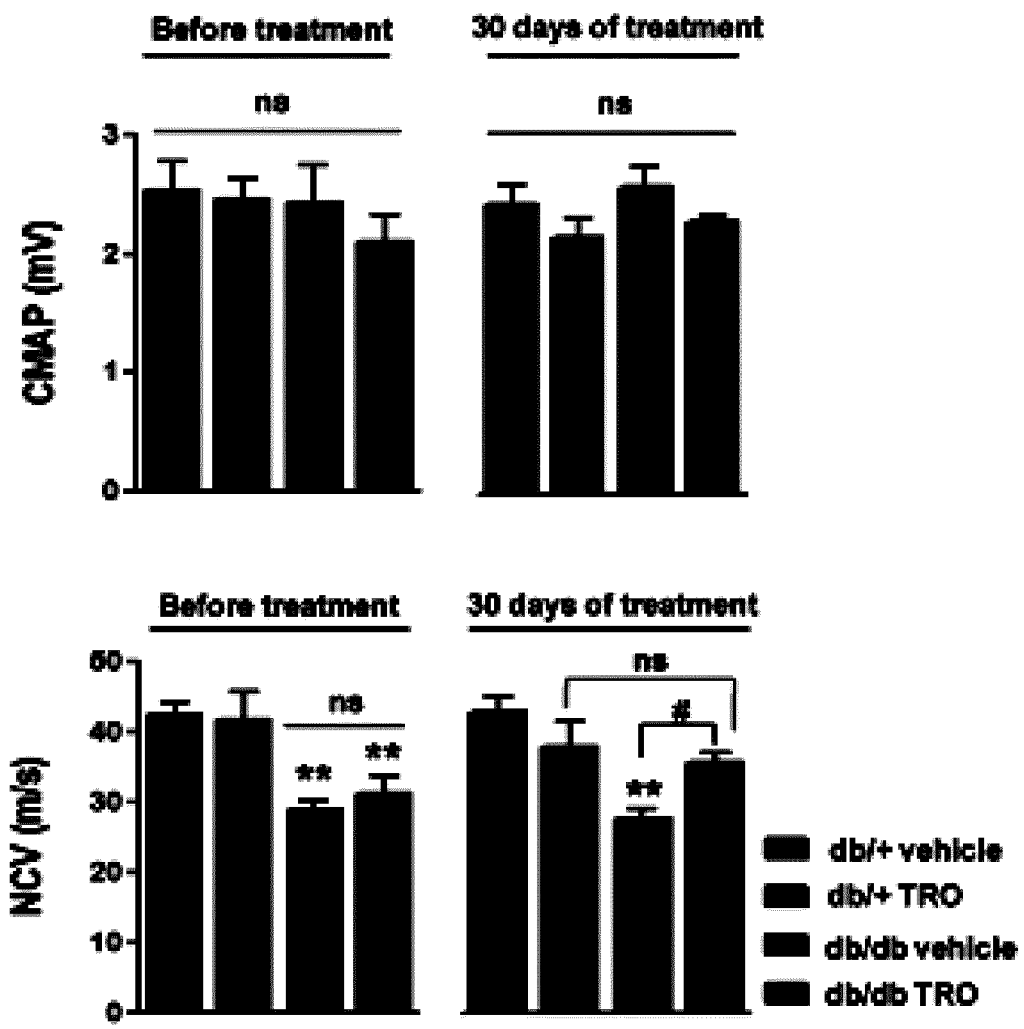

5 Claims, 6 Drawing Sheets
Specification includes a Sequence Listing.

SEQUENCE LISTING

```
<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Synthetic sh RNA

<400> SEQUENCE: 1
agttccagta cggctccaa                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic sh RNA

<400> SEQUENCE: 2
caagctgacc ctgaagttc                                                    19

<210> SEQ ID NO 3
<211> LENGTH: 21
<212> TYPE: DNA
<213> ORGANISM: Artificial Sequence
<220> FEATURE:
<223> OTHER INFORMATION: Synthetic sh Rna

<400> SEQUENCE: 3
gcctggaaac caagtacaga t                                                 21

<210> SEQ ID NO 4
<211> LENGTH: 23
<212> TYPE: DNA
<213> ORGANISM: Artificial Sequence
<220> FEATURE:
<223> OTHER INFORMATION: Synthetic sh RNA

<400> SEQUENCE: 4
gttggctata agacggatga act                                               23

<210> SEQ ID NO 5
<211> LENGTH: 23
<212> TYPE: DNA
<213> ORGANISM: Artificial Sequence
<220> FEATURE:
<223> OTHER INFORMATION: Synthetic sh RNA

<400> SEQUENCE: 5
accaggtatc aaactgacgt tct                                               23
```

```
<210> SEQ ID NO 6
<211> LENGTH: 22
<212> TYPE: DNA
<213> ORGANISM: Artificial Sequence
<220> FEATURE:
<223> OTHER INFORMATION: Synthetic sh RNA

<400> SEQUENCE: 6
agttgataaa taccacgtta ct                                              22

<210> SEQ ID NO 7
<211> LENGTH: 23
<212> TYPE: DNA
<213> ORGANISM: Artificial Sequence
<220> FEATURE:
<223> OTHER INFORMATION: Synthetic sh RNA

<400> SEQUENCE: 7
gctacggctt tggcttaata act                                             23
```

METHODS AND PHARMACEUTICAL COMPOSITIONS FOR TREATING PERIPHERAL DEMYELINATING DISEASES

FIELD OF THE INVENTION

The present invention relates to methods and pharmaceutical compositions for treating peripheral demyelinating diseases.

BACKGROUND OF THE INVENTION

The Schwann cells (SC) are responsible of myelin production in peripheral nervous system. These cells wrap the axons and remain associated to protect them and allow the correct and efficient action potential transmission[1,2]. Unfortunately, hereditary and acquired demyelinating diseases of the peripheral nervous system (PNS) are numerous and affect an increasing number of people[3].

Acquired demyelinating diseases are even more common as they include diabetic peripheral neuropathy[4], drug-related peripheral demyelinating diseases, leprosy and peripheral demyelinating diseases of inflammatory etiology[5]. Demyelinating peripheral neuropathy is a major complication of diabetes and a cause of considerable morbidity[6]. This neuropathy is characterized by the loss and/or degeneration of neurons and Schwann cells, and the slowing of nerve conduction velocities[7,8]. Moreover, it has been reported that at least 50% of diabetic patients develop one or several forms of diabetic neuropathies within 25 years after diagnosis[9].

In the PNS, hereditary demyelinating diseases are rare but remain among the most common hereditary diseases[10]. While they are rarely lethal, they range from life threatening to severely affecting life and therefore put a high burden on public health systems. The most common of these diseases are termed as Charcot-Marie-Tooth (CMT) diseases[10]. Numerous genes mutated in these diseases are known but the molecular mechanisms that they affect often remain unclear[11].

The etiologies of all these acquired and hereditary peripheral diseases are diverse but they all result in demyelination. Thus an important challenge is to understand the cellular and molecular events that underlie myelination and demyelination. In this way, recent studies show that mitochondria dysfunctions are involved in an increasing number of demyelinating neurodegenerative diseases[12,13]. Myelin sheath mitochondria have been shown to be essential for neuron homeostasis[14] but their morphological and physiological properties remain elusive. It is well known that patients suffering from mitochondrial multisystem disorders often show a peripheral neuropathy in addition to other more debilitating symptoms[12,15]. Myelinating Schwann cells (mSC) of patients suffering these diseases display features of demyelination as well as abnormal mitochondria. More directly, some acquired demyelinating PNS diseases appear to be linked to defects in mitochondrial functions. For example diabetes and the treatment with some drugs such as amiodarone, perhexiline, Tacrolimus have been linked with perturbation of mitochondrial functions and to mitochondrial stress. Consistently, one of the main side effect of these drugs and the main comorbidity associated with diabetes is demyelinating peripheral neuropathy[16].

SUMMARY OF THE INVENTION

The present invention relates to methods and pharmaceutical compositions for treating peripheral demyelinating diseases. In particular, the present invention is defined by the claims.

DETAILED DESCRIPTION OF THE INVENTION

The formation of the myelin sheath around peripheral nerve axons by Schwann cells is essential for the rapid propagation of action potentials. A large number of peripheral neuropathies have as pathological physiology a process of demyelination. Whereas the molecular mechanism that activates and regulates this process remains unclear, some studies suggest that Schwann cell mitochondria could play an essential role in demyelination process. Here the inventors show, using in vivo imaging and viral approaches, that calcium released by mitochondrial VDAC1 directly induces Schwann cell demyelination via MAPK and c-jun activation after sciatic nerve injury and more importantly in diabetic neuropathy. Moreover, reduction of mitochondrial calcium release by VDAC1 silence or/and drug blocking strongly reduces the number of demyelinating Schwann cell in vivo and improve nerve conduction and neuromuscular activity in diabetic and Charcot-Marie Tooth disease models.

Accordingly the present invention relates to a method of treating a peripheral demyelinating disease in a subject in need thereof comprising administering to the subject a therapeutically effective amount of an inhibitor of VDAC1 activity or expression.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

The method of the present invention has wide applicability to the treatment or prophylaxis of peripheral demyelinating diseases affecting the regulation of peripheral nerves including peripheral ganglionic neurons, sympathetic, sensory neurons, and motor neurons. In particular, the method of the present invention is useful in treatments designed to rescue, for example, retinal ganglia, inner ear and accoustical nerves, and motorneurons. In particular, the method of the present invention is particularly suitable for preventing peripheral nerve demyelination. The wide variety of morphologies exhibited by peripheral demyelinating diseases can each be uniquely attributed to an equally wide variety of causes. For instance, peripheral demyelinating diseases can be genetically acquired ("hereditary peripheral demyelinating diseases"), or can result from a systemic disease, or can be induced by a toxic agent or an infectious agent ("acquired peripheral demyelinating diseases").

In some embodiments, the method of the present invention is suitable for the treatment of hereditary peripheral demyelinating diseases. Hereditary peripheral demyelinating diseases are caused by genetic abnormalities which are transmitted from generation to generation. For several of these, the genetic defect is known, and tests are available for diagnosis and prenatal counseling. In particular, the diagnosis of a hereditary peripheral demyelinating disease is usually suggested with the early onset of neuropathic symptoms, especially when a positive family history is also present. Prior to the recent genetic advances, the diagnosis was supported by typical findings of marked slowing of the nerve conduction studies on electromyography and a nerve biopsy. Typical findings on a nerve biopsy include the presence of so-called onion-bulbs, indicating a recurring demyelinating and remyelinating of the nerve fibers. There are a number of hereditary demyelinating neuropathies. Examples include but are not limited to Refsum's disease, Abetalipoproteinemia, Tangier disease, Krabbe's disease, Metachromatic leukodystrophy, Fabry's disease, Dejerine-Sottas syndrome,—and others. Of all the hereditary peripheral demyelinating diseases, the most common by far is Charcot-Marie-Tooth Diseases. Charcot-Marie-Tooth (CMT) Diseases are the most common hereditary neurological disorders. It is characterized by weakness and atrophy of muscles due to segmental demyelination of peripheral nerves and associated degeneration of axons and anterior horn cells. During the last 15 years, there has been a substantive increase in knowledge about the genetic basis of Charcot-Marie-Tooth disease (CMT) with over 60 genes known at present. A regularly updated list can be found at http://www.molgen.ua.ac.be/CMTMutations/Home/IP-N.cfm. Autosomal dominant inheritance is usual, and associated degenerative CNS disorders, such as Friedreich's ataxia, are common. In some embodiments, the method of the present invention can be used for the treatment of Charcot-Marie-Tooth disease type 4F. In some embodiments, the method of the present invention can be used to treat, or at least reduce the severity of Amyotrophic lateral sclerosis (ALS). In some embodiments, the method of the present invention can be used in the treatment of Familial Amyloidotic Neuropathy and other related hereditary peripheral demyelinating diseases. The method of the present invention can be used in the treatment of hereditary *porphyria*, which can have components of peripheral neuropathy. Still another hereditary peripheral demyelinating disease for which the method of the present inventions can be used for treatment is hereditary sensory neuropathy Type II (HSN II). In some embodiments, the method of the present invent can be used for the treatment of certain muscular dystrophies. In some embodiments, the method of the present invention can be used for the treatment of congenital muscular dystrophy 1A.

The method of the present invention is also suitable the treatment of acquired peripheral demyelinating diseases.

In some embodiments, the method of the present invention is suitable for the treatment of diabetic neuropathies. Diabetes is the most common known cause of neuropathy. It produces symptoms in approximately 10% of people with diabetes. In most cases, the neuropathy is predominantly sensory, with pain and sensory loss in the hands and feet. But some diabetics have mononeuritis or mononeuritis multiplex which causes weakness in one or more nerves, or lumbosacral plexopathy or amyotrophy which causes weakness in the legs.

In some embodiments, the method of the present invention can also be used in the treatment of immune-mediated neuropathies. The main function of the immune system is to protect the body against infectious organisms which enter from outside. In some cases, however the immune system turns against the body and causes autoimmune disease. The immune system consists of several types of white blood cells, including T-lymphocytes, which also regulate the immune response; and B-lymphocytes or plasma cells, which secrete specialized proteins called "antibodies" Sometimes, for unknown reasons, the immune system mistakenly attacks parts of the body such as the peripheral nerves. This is "autoimmune" Peripheral Neuropathy. There are several different types, depending on the part of the peripheral nerve which is attacked and the type of the immune reaction. For instance, the method of the present invention is suitable for treating Guillain-Barre Syndrome (GBS). An acute neuropathy because it comes on suddenly or rapidly. Guillain-Barre Syndrome can progress to paralysis and respiratory failure within days or weeks after onset. The neuropathy is caused when the immune system destroys the myelin sheaths of the motor and sensory nerves. It is often preceded by infection, vaccination or trauma, and that is thought to be what triggers the autoimmune reaction. The disease is self-limiting, with spontaneous recovery within six to eight weeks. But the recovery is often incomplete.

Other acquired peripheral demyelinating diseases which begin acutely, and which can be treated by the method of the present invention, include Acute Motor Neuropathy, Acute Sensory Neuropathy, and Acute Autonomic Neuropathy, in which there is an immune attack against the motor, sensory or autonomic nerves, respectively. The Miller-Fisher Syndrome is another variant in which there is paralysis of eye gaze, incoordination, and unsteady gait Still another acquired peripheral demyelinating disease which is may be treated by the method of the present invention is Chronic Inflammatory Demyelinating Polyneuropathy (CIDP). CIDP is thought to be a chronic and more indolent form of the Guillain-Barre Syndrome. The disease progresses either with repeated attacks, called relapses, or in a stepwise or steady fashion. As in GBS, there appears to be destruction of the myelin sheath by antibodies and T-lymphocytes. But since there is no specific test for CIDP, the diagnosis is based on the clinical and laboratory characteristics.

Chronic Polyneuropathies with antibodies to peripheral nerves is still another peripheral demyelinating diseases for which the method of the present inventions can be employed to treat. In some types of chronic neuropathies, antibodies to specific components of nerve have been identified. These include demyelinating peripheral disease associated with antibodies to the Myelin Associated Glycoprotein (MAG), motor neuropathy associated with antibodies to the gangliosides GM1 or GD1a, and sensory neuropathy associated with anti-sulfatide or GD1b ganglioside antibodies. The antibodies in these cases bind to oligosaccharide or sugar like molecules, which are linked to proteins (glycoproteins) or lipids (glycolipids or gangliosides) in the nerves.

The method of the present invention can also be used as part of a therapeutic plan for treating peripheral demyelinating diseases associated with vasculitis or inflammation of the blood vessels in peripheral nerves. Peripheral demyelinating disease can also be caused by Vasculitis—an inflammation of the blood vessels in peripheral nerve. It produces small "strokes" along the course of the peripheral nerves, and may be restricted to the nerves or it may be generalized, include a skin rash, or involve other organs. Several rheumatological diseases like Rheumatoid Arthritis, Lupus, Periarteritis Nodosa, or Sjogren's Syndrome, are associated with generalized Vasculitis, which can also involve the peripheral nerves. Vasculitis can cause Polyneuritis, Mononeuritis, or Mononeuritis Multiplex, depending on the distribution and severity of the lesions.

In some embodiments, the method of the present invention is suitable for the treatment of peripheral demylinating diseases associated with monoclonal gammopathies. In Monoclonal Gammopathy, single clones of B-cells or plasma cells in the bone marrow or lymphoid organs expand to form benign or malignant tumors and secrete antibodies. "Monoclonal" is because there are single clones of antibodies. And "Gammopathy" stands for gammaglobulins, which is another name for antibodies. In some cases, the antibodies react with nerve components; in others, fragments of the antibodies form amyloid deposits.

In some embodiments, the method of the present invention is suitable for the treatment of peripheral demyelinating diseases associated with tumors or neoplasms. Neuropathy can be due to direct infiltration of nerves by tumor cells or to indirect effect of the tumor. The latter is called Paraneoplastic Neuropathy. Several types have been described. For instance, the method of the present inventions can be used to manage sensory neuropathy associated with lung cancer. Likewise, the method of the present invention can be used to treat peripheral demyelinating diseases associated with multiple myeloma. In some embodiments, the method of the present invention is suitable for the treatment of peripheral demyelinating diseases associated with Waldenstrom's Macroglobulemia, Chronic Lymphocytic Leukemia, or B-cell Lymphoma. In some embodiments, the method of the present invention is used as part of therapeutic protocol for the treatment of patients with cancers where peripheral demyelinating disease is a consequence of local irradiation or be caused by a chemotherapeutic agent. Chemotherapeutic agents known to cause sensory and/or motor neuropathies include vincristine, an antineoplastic drug used to treat haematological malignancies and sarcomas, as well as cisplatin, taxol and others. The neurotoxicity is dose-related, and exhibits as reduced intestinal motility and peripheral neuropathy, especially in the distal muscles of the hands and feet, postural hypotension, and atony of the urinary bladder. Similar problems have been documented with taxol and cisplatin (MoUman, J. E., 1990, New Eng Jour Med. 322: 126-127), although cisplatin-related neurotoxicity can be alleviated with nerve growth factor (NGF) (Apfel, S. C. et al, 1992, Annals of Neurology 31:76-80). Although the neurotoxicity is sometimes reversible after removal of the neuro toxic agent, recovery can be a very slow process (Legha, S., 1986, Medical Toxicology 1:421-427; Olesen, et al, 1991, Drug Safety 6:302-314).

In some embodiments, the method of the present invention is suitable for the treatment of peripheral demyelinating diseases caused by a drug such as Chloroquine, FK506 (Tacrolimus), Perhexiline, Procainamide and Zimeldine.

In some embodiments, the method of the present invention is suitable for the treatment of peripheral demyelinating diseases caused by infections. Peripheral demyelinating diseases can be caused by infection of the peripheral nerves. Viruses that cause peripheral demyelinating diseases include the AIDS virus, HIV-I, which causes slowly progressive sensory neuropathy, Cytomegalovirus which causes a rapidly progressive paralytic neuropathy, Herpes Zoster which cause Shingles, and Poliovirus which causes a motor neuropathy. Hepatitis B or C infections are sometimes associated with vasculitic neuropathy. Bacterial infections that cause neuropathy include Leprosy which causes a patchy sensory neuropathy, and Diphtheria which can cause a rapidly progressive paralytic neuropathy. Other infectious diseases that cause neuropathy include Lyme disease which is caused by a spirochete, and Trypanosomiasis which is caused by a parasite. Both commonly present with a multifocal neuropathy In some embodiments, the method of the present invention is suitable for the treatment of peripheral demyelinating diseases caused by nutritional imbalance. Deficiencies of Vitamins B12, B1 (thiamine), B6 (pyridoxine), or E, for example, can produce polyneuropathies with degeneration of peripheral nerve axons. This can be due to poor diet, or inability to absorb the nutrients from the stomach or gut. Moreover megadoses of Vitamin B6 can also cause a peripheral demyelinating disease, and the method of the present invention can be used as part of a de-toxification program in such cases.

In some embodiments, the method of the present invention is suitable for the treatment of peripheral demyelinating diseases arising in kidney diseases. Chronic renal failure can cause a predominantly sensory peripheral neuropathy with degeneration of peripheral nerve axons.

In some embodiments, the method of the present invention is suitable for the treatment of hypothyroid neuropathies. Hypothyroidism is sometimes associated with a painful sensory polyneuropathy with axonal degeneration. Mononeuropathy or Mononeuropathy Multiplex can also occur due to compression of the peripheral nerves by swollen tissues.

In some embodiments, the method of the present invention is suitable for the treatment of peripheral demyelinating diseases caused by Alcohol and Toxins. Certain toxins can cause Peripheral Neuropathy. Lead toxicity is associated with a motor neuropathy; arsenic or mercury cause a sensory neuropathy, Thalium can cause a sensory and autonomic neuropathy, several of the organic solvents and insecticides can also cause polyneuropathy. Alcohol is directly toxic to nerves and alcohol abuse is a major cause of neuropathy. The method of the present invention can be used, in some embodiments, as part of a broader detoxification program. In still another embodiment, the method of the present invention can be used for the treatment of peripheral demyelinating diseases caused by drugs. Several drugs are known to cause neuropathy. They include, among others, nitrofurantoin, which is used in pyelonephritis, amiodarone in cardiac arrhythmias, disulfiram in alcoholism, ddC and ddI in AIDS, and dapsone which is used to treat Leprosy. As above, the method of the present invention can be used, in some embodiments, as part of a broader detoxification program.

In some embodiments, the method of the present invention is suitable for the treatment of peripheral demyelinating diseases caused by trauma or compression. Localized neuropathies can result from compression of nerves by external pressure or overlying tendons and other tissues. The best known of these are the Carpal Tunnel Syndrome which results from compression at the wrist, and cervical or lumbar radiculopathies (Sciatica) which result from compression of nerve roots as they exit the spine. Other common areas of nerve compression include the elbows, armpits, and the back of the knees.

The method of the present invention is also useful in variety of idiopathic peripheral demyelinating diseases. The term "idiopathic" is used whenever the cause of the peripheral demyelinating disease cannot be found. In these cases, the peripheral demyelinating disease is classified according to its manifestations, i.e., sensory, motor, or sensorimotor idiopathic polyneuropathy.

As used herein, the term "VDAC1" has its general meaning in the art and refers to the voltage-dependent anion-selective channel protein 1. VDAC1 is a major component of the outer mitochondrial membrane which facilitates the exchange of metabolites and ions across the outer mitochondrial membrane and may regulate mitochondrial functions. This protein also forms channels in the plasma membrane and may be involved in transmembrane electron transport. Alternate splicing results in multiple transcript variants.

As used herein the term "inhibitor of VDAC1" refers to any compound capable to inhibit the activity of VDAC1.

In some embodiments, the inhibitor of VDAC1 activity is olesoxime (TRO19622) (WO2004082581). The exact name of olesoxime is (NZ)—N-[(8S,9S,10R,13R,14S,17R)-10,13-dimethyl-17-[(2R)-6-methylheptan-2-yl]-1,2,6,7,8,9,11,12,14,15,16,17-dodecahydrocyclopenta[a]phenanthren-3-ylidene]hydroxylamine and has the general formula of:

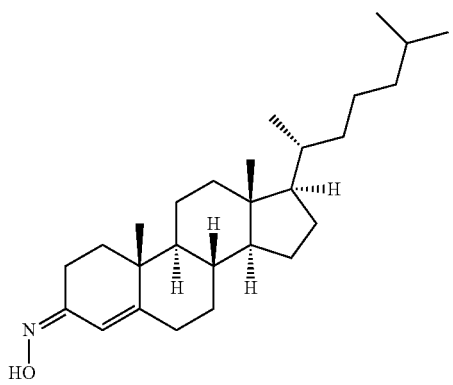

An "inhibitor of expression" refers to a natural or synthetic compound that has a biological effect to inhibit the expression of a gene. For example, an "inhibitor of expression" denotes a natural or synthetic compound that has a biological effect to inhibit the expression of the targeted gene.

Inhibitors of gene expression for use in the present invention may be based on antisense oligonucleotide constructs. Anti-sense oligonucleotides, including anti-sense RNA molecules and anti-sense DNA molecules, would act to directly block the translation of the targeted mRNA by binding thereto and thus preventing protein translation or increasing mRNA degradation, thus decreasing the level of the targeted protein, and thus activity, in a cell. For example, antisense oligonucleotides of at least about 15 bases and complementary to unique regions of the mRNA transcript sequence encoding the target protein can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of gene expression for use in the present invention. Gene expression can be reduced by contacting the tumor, subject or cell with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of the targeted mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art. Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991). Preferred viruses for certain applications are the adeno-viruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

As used herein, the term "effective amount" refers to a quantity sufficient to achieve a therapeutic effect (e.g. preventing demyelination). In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. In some embodiments, an effective amount of the inhibitor of VDAC1 activity or expression for achieving a therapeutic or prophylactic effect, range from about 0.000001 mg per kilogram body weight per day to about 10,000 mg per kilogram body weight per day. Typically, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In some embodiments, a single dosage of peptide ranges from 0.1-10,000 micrograms per kg body weight. In some embodiments, aromatic-cationic peptide concentrations in a carrier range from 0.2 to 2000 micrograms per delivered milliliter.

Typically, the inhibitor of VDAC1 activity or expression is combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Sterile injectable solutions are prepared by incorporating the inhibitor signaling pathway in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

A further aspect of the present invention relates to a method for screening a drug for the treatment of peripheral demyelinating diseases comprising the steps of i) providing a test compound, ii) determining whether the test compound is able to inhibit VDAC1 activity or expression and iii) positively selecting the test compound when it inhibits VDAC1 activity or expression.

In some embodiments, the screening method of the invention is performed in a Schwann cell.

In some embodiments, the screening method of the invention comprises the steps of determining whether the test compound is able to bind to VDAC1. Any method well known in the art for determining whether the test compound is able to bind to VDAC1 may be used. In some embodiments, the screening method of the invention comprises the step of determining whether the test compound is able to inhibit the calcium releasing by mitochondrial VDAC1. In particular, the screening method of the invention comprises the step of determining whether the test compound is able to inhibit MAPK and c-jun activation by VDAC1.

The above assays may be performed using high throughput screening techniques for identifying test compounds for developing drugs that may be useful to the treatment of peripheral demyelinating diseases. High throughput screening techniques may be carried out using multi-well plates (e.g., 96-, 389-, or 1536-well plates), in order to carry out multiple assays using an automated robotic system. Thus, large libraries of test compounds may be assayed in a highly efficient manner. Compounds in the library will be applied one at a time in an automated fashion to the wells of the microtitre dishes containing the transgenic cells described above. The whole cell assay of the invention described herein can be performed, for example, by utilizing pre-packaged kits comprising any or all of the reagents of the assay, such as a solid phase coated with a binding partner to a protein of interest, or a detection molecule. The cell-free assays of the invention may be performed, for example, by utilizing pre-packaged kits comprising any or all of the reagents of the assay.

In some embodiments, the screening method of the invention comprises a step of performing a functional assay. In some embodiments, an in vitro myelination model as described in the EXAMPLE may be used. For examples the test compound is put in contact with non-elongating myelinating cells in culture and production of myelin is then measured. It is then possible to positively select test compound that are able to produce an increased amount of myelin (in comparison with a control cells which are not put in contact with the test compound). In vivo assays may also be performed as described in the EXAMPLE.

In some embodiments, the test compound of may be selected from the group consisting of peptides, peptidomimetics, small organic molecules, antibodies, aptamers or nucleic acids. For example the test compound according to the invention may be selected from a library of compounds previously synthesized, or a library of compounds for which the structure is determined in a database, or from a library of compounds that have been synthesized de novo. In a particular embodiment, the test compound may be selected form small organic molecules. As used herein, the term "small organic molecule" refers to a molecule of size comparable to those organic molecules generally sued in pharmaceuticals. The term excludes biological macromolecules (e.g.; proteins, nucleic acids, etc.); preferred small organic molecules range in size up to 2000 Da, and most preferably up to about 1000 Da.

The invention will be further illustrated by the following figures and examples. However, these examples and figures should not be interpreted in any way as limiting the scope of the present invention.

FIGURES

FIG. 1. Myelin sheath recovering in diabetic mice by VDAC1 silencing or blocking.

(A) Quantification of the CMAP (top) and NCV (bottom). Error bars indicate SEM. Asterisks mark statistical differences over control mice and hashes mark statistical differences over diabetic mice treated with vehicle. ns marks non-statistical differences compared control mouse. Statistical significances were determined using a two-tailed Student's t test. $^\#P<0.05$ and $**P<0.01$ (B) Grip strength (top panel) and rotarod latency (bottom panel) of control (db/+) and diabetic (db/db) mice during 30 days of vehicle or TRO 19622 treatment. n=12 mice for each group. Asterisks mark statistical differences over control mouse latency and hashes mark statistical differences over diabetic mice treated with vehicle. Discontinuous lines and error bars indicate SEM. Statistical significances were determined using one-way ANOVA followed by a Dunnett's multiple comparison post hoc test. Error bars indicate SEM. * and $^\#P<0.05$, ** and $^{\#\#}P<0.01$.

FIG. 2. Reduction of demyelination and increase of neuromuscular performance in CMT1A rat model by VDAC1 blocking (A) All-limb (front and hind limbs) grip strength analysis of control (wt) and CMT1A rats during 30 days of vehicle or TRO 19622 treatment. Paw stand (B), distance between paws (C) and paw print area (D) of control (wt) and CMT1A rats during 30 days of vehicle or TRO 19622 treatment determined using Catwalk XT 10.5 test system. n=6 rats for each group. Statistical significances were determined using one-way ANOVA followed by a Dunnett's multiple comparison post hoc test. Asterisks mark statistical differences over control mice and hashes mark statistical over CMT1A rats treated with vehicle. Error bars indicate SEM. * and $^\#P<0.05$, ** and $^{\#\#}P<0.01$.

EXAMPLE

Material & Methods

Animal Housing

Immunodeficient strain CB17/SCID mice (Janvier Labs, France), diabetic mice (Homozygous BKS(D)-Lepr$^{db+/+}$/JOrlRj) (Janvier Labs, France) and their controls (Heterozygous BKS(D)-Lepr$^{db+/-}$/JOrlRj) (Janvier Labs, France) were kept in the A2 animal house facility whereas the transgenic pmp22 CMT1A rats (kindly provided by Dr. M. Sereda, Göttingen, Germany) were housed in the A1 animal house facility of the Institute for Neurosciences of Montpellier in ventilated and clear plastic boxes, subjected to standard light cycles (12 h to 90 lux light, 12 h dark). The care, breeding and use of animals followed the animal welfare guidelines of the "Institut National de la Santé et de la Recherche Medicale" (INSERM), under the approval of the French "Ministère de l'Alimentation, de l'Agriculture et de la Pêche". All experiments using animals were performed in accordance with all institution and government ethics and animal handling requirements. (French Institutional and National Regulation Approval Number CEEA-LR-11032).

Cloning

The DNA for the fluorescent protein mito-dsRed2 (Clontech) was cut using NheI and NotI enzymes and then, treated with DNA polymerase I Large Klenow fragment. After purification, it was cloned into pAdtrack-CMV (Quantum Biotechnologies, Inc.) or pAAV-MCS (Cell Biolabs, Inc.) plasmids under the control of a CMV or a CAG promoter respectively. The fluorescent probe mito-GCaMP2 (kindly provided by Dr. X. Wang, Peking University, China) cloned into a pcDNA3.1 was cut using HindIII and EcoRV to be cloned into a pShuttle-CMV (Quantum Biotechnologies, Inc.) or with BamHI and EcoRV to be cloned into a pAAV-MCS vector under the control of a CMV or a CAG promoter respectively. Then, the GCaMP2 probe (without mito sequence) was cut using HindIII and EcoRV to be cloned into a pAAV-MCS and pShuttle-CMV vector. The probe mito-SypHer (kindly provided by Dr. J. C. Jonas, Université Catholique de Louvain, Belgium) was cut using NheI and NotI enzymes and then, treated with DNA polymerase I Large Klenow fragment. After purification, it was cloned into pAAV-MCS under the control of a CAG promoter. The VDAC1 shRNA sequence 2 GTTGGCTATAAGACGGATGAACT (Sigma-Aldrich, Ref. #TRCN0000012391), the VDAC1 shRNA sequence 3 ACCAGGTATCAAACTGACGTTCT (Sigma-Aldrich, Ref. #TRCN0000012392) or the shRNA control (dsRed2) AGTTCCAGTACGGCTCCAA or (GFP) CAAGCTGACCCTGAAGTTC were first cloned separately into a pSicoR vector (Addgene, Ref 11579) under the control of a U6 promoter using HpaI and BstEII enzymes then, the U6-VDAC1-shRNA sequences were cut using ApaI and BstEI to be cloned into a pAAV-CMV-GFP vector (Cell Biolabs, Inc.), the pAAV-mito-GCaMP2, the pAAV-GCaMP2, the pAAV-mito-dsRed2 or the pAAV-mito-SypHer previously described. All clones were validated by sequencing.

Cell Culture

HEK (human embryonic kidney)-293T or immoral mouse Schwann cells were grown in DMEM (Dulbecco's modified Eagle's medium) (Gibco Life Technologies) supplemented with 2 mM L-glutamine, 100 U ml$^{-1}$ penicillin/streptomycin and 5% (v/v) heat-inactivated fetal bovine serum (all supplements were from Invitrogen). Cells were maintained at 37° C. in an atmosphere of 5% $CO_2$, and were passaged when they were 80-90% confluent, twice a week.

shRNA mSC Transfection

Five 15 cm dishes of 70-80% confluent mouse Schwann cells were separately transfected with 30 µg of pLKO.1-puro vector containing five commercial VDAC1 shRNA (Sigma-Aldrich, #TRCN0000012388 #TRCN0000012389 #TRCN0000012390 #TRCN0000012391 #TRCN0000012392) using 80 µl of Lipofectamine 2000 (Invitrogen) and 1.5 ml of Opti-Mem (Gibco Life Technologies). After 7 h, the medium was changed to a fresh complete culture medium enriched with 2 mM of glutamine. 48 h after, transfected cells were treated with 0.5 µg/ml of Puromycin (Gibco Life Technologies) for cell selection. Antibiotic was maintained in cell medium during one week. Then, cells were collected for western blot.

Protein Extraction and Western Blotting.

Transfected cells with VDAC1-shRNA were washed in PBS, lysed in lysis buffer (10 mM Tris, pH 7.4, 150 mM NaCl, 1% Triton X-100, 0.1% SDS, 0.5% sodium-deoxycholate, 1 mM EDTA, 50 mM NaF, 1 mM NaVO4, protease inhibitor cocktail (Sigma-Aldrich)) for 15 min on ice, and centrifuged at 14,000 rpm at 4° C. to pellet cell debris. Sciatic nerves were dissected from mice, washed in PBS and directly fixed with 4% of PFA for 10 minutes. After removal of the epineurium and perineurium, the nerves were homogenized by sonication in lysis buffer. Cellular debris was removed by centrifugation at 13,000 g for 5 min at 4° C. and protein was quantified by the bicinchoninic acid method using bovine serum albumin as a standard. Then, samples were denatured at 98° C., loaded on 10% SDS-PAGE, and transferred to PVDF membranes for immunoblotting. Antibody against the phospho-563-c-jun was mouse (1/100, BD Biosciences, Ref. 558036) and antibodies against VDAC (1/1000, Cell Signaling, Ref. 4866), phospho-Thr183/Tyr185-SAPK/JNK (1/1000, Cell Signaling, Ref. 9251), phospho-Thr202/Tyr204-p44/42 MAPK (Erk 1/2) (1/1000, Cell Signaling, Ref. 9101), phospho-Thr180/Tyr182-p38 (1/1000, Cell Signaling, Ref. 9211), Cleaved Caspase-3 (1/1000, Cell Signaling, Ref. 9661) were rabbit. And antibody against phospho-587-bcl2 was goat (1/500, Santa Cruz Biotechnology, Ref. sc-16323).

Viral Particles Production

Adenoviral particles production was described in He et al., 1998[1]. Briefly, for adenovirus production pAdtrack vector containing the constructs was recombined with pAdeasyl vector in the Adeasyl BJ5183 bacteria strain (Stratagene). The isolated adenoviral DNA was cut with Pad enzyme and transfected in HEK 293 cells using Lipofectamine 2000. The first production of adenovirus is followed by 3 rounds of amplification. Finally freeze thaw cycles are used to harvest the viral particles from the cells which are then purified using cesium chloride gradients. To produce high-titer adeno-associated virus (AAV10), three 15 cm dishes of 70-80% confluent HEK293T cells were transfected with 71 µg of pAAV expression vector, 20 µg of pAAV10 capsid and 40 µg of pHelper (Cell Biolabs, Inc.). 48 h later transfection, the medium was collected, pooled and centrifuged 15 min at 2000 rpm to spin down floating cells. In parallel, cells were scraped and collected in PBS. Then, cells were lysed using dry ice/ethanol bath and centrifuged 15 min at 5000 rpm to discard cell debris. The cleared supernatant and the cleared medium were pooled and filtrated using a 0.22 µm filter. The viral solution was filtrated through a cation-exchange membrane Mustang S acrodisc (Pall Corporation) to deplete empty particles and later, filtrated through an anion-exchange membrane Mustang Q acrodisc (Pall corporation) to retain AAV viral particles. Then, viruses were eluted and concentrated using centrifugal concentrators Amicon tube. Usual titer is around $10^{11}$ PFU/ml. (for further details see Okada et al., 2009[2])

In Vivo Virus Injection in the Sciatic Nerve

Mice were anesthetized with isoflurane inhalation and placed under a Stemi2000 microscope (Zeiss). Incision area was shaved and cleaned using betadine solution. After incision, the gluteus superficialis and biceps femoris muscles were separated to reveal the cavity traversed by the sciatic nerve. The nerve was lift out using spatula and a thin glass needle filled with viral solution (8 µl) was introduced into the nerve with a micromanipulator. This solution was injected over 30 min with short pressure pulses using a Picospritzer III (Parker Hannifin) coupled to a pulse generator. After injection, the nerve was replaced into the cavity, the muscles were readjusted, and the wound was closed using clips (for further details see Gonzalez et al., 2014[3]).

Immunohistochemistry

The dissected nerve was washed in L15 medium, fixed in Zamboni's fixative (Stefanini et al., 1967[4]) for 10 min at room temperature, washed in PBS, and incubated in successive glycerol baths (15, 45, 60, 66% in PBS) for 18 to 24 h each before freezing at −20° C. The nerves were cut in small pieces in 66% glycerol and the perineurium sheet removed. Small bundles of fibers were teased in double-distilled water on Superfrost slides, dried overnight at room temperature, and the slides stored at −20° C. For immunostaining, the teased fibers were incubated for 1 h at room temperature in blocking solution (10% goat serum, 0.2% TritonX100, and 0.01% sodium azide in PBS). Then, the samples were then incubated with anti-ECCD2 primary mouse antibody (1/100, BD biosciences, Ref. 610181), anti-phosphoS63-c-jun primary mouse antibody (1/200, BD Biosciences, Ref. 558036), anti-c-jun primary mouse antibody (1/200, BD Biosciences, Ref. 610326), anti-VDAC primary rabbit antibody (1/100, Cell Signaling, Ref. 4866) or/and MitoTracker Red (1/1000, Molecular Probes, Ref. M7515) in blocking solution overnight at 4° C. The next day, the samples were washed in PBS and incubated for 1 h at room temperature with secondary donkey antibodies coupled to Alexa488, Alexa 594 or Alexa647 (1/1600, Molecular probes) and TO-PRO-3 iodide (50 µM, Invitroge, Ref. T3605). Finally the samples were washed in PBS and mounted in Immu-mount (Thermo Scientific). Images were acquired at room temperature using a 20× or 40× objective, a Zeiss confocal microscope LSM710, and its associated software.

Drug Administration

TRO19622 drug (Tocris bioscience, Ref. 2906) was diluted in ethanol to 20 mM and then, the solution was diluted in sterile PBS to 20 µM. TRO19622 treatments were realized by 3 mg/kg intraperitoneal (IP) injections of 20 mM solution or by intra sciatic nerve injections of 2 µl of drug solution 2 µM using a Hamilton syringe or a glass needle in sterile conditions 30 minutes before multiphoton image acquisitions or immunohistochemistry and demyelination studies respectively. Methyl jasmonate drug (Sigma-Aldrich, Ref. 392707) was diluted in 1 ml of sterile PBS to 1M or 3M. Methyl jasmonate treatments were realized by intra sciatic nerve injections of 1 µl of drug solution using a glass needle and micromanipulator in sterile conditions following the same virus injections procedure (see in vivo virus injection in the sciatic nerve method) two hours before multiphoton image acquisition. Cyclosporin A (Sigma Aldrich, Ref. 30024-25MG) was previously diluted to 50 mM in ethanol and then, the solution was diluted in sterile PBS to 0.2 µM and 50 µM. Cyclosporin A treatments were realized by intra sciatic nerve injections of 4 µl of solutions using a glass needle and micromanipulator in sterile conditions 30 minutes before multiphoton image acquisitions. Ethanol for TRO19622 or PBS for methyl jasmonate and Cyclosporin A were used as vehicle. All drug concentrations were previously evaluated by Bordet et al, 2007[5]; Goldin et al, 2008[6]; Sharov et al, 2007[7].

Ketamine/Xylazine Anesthesia 1 ml of ketamine-HCl (100 mg/ml, IMALGEN, Merial Lab) and 0.1 ml of xylazine-HCl (100 mg/ml, ROMPUN, Bayer Sante) were mixed in a sterile tube with 8.9 ml of sterile PBS. The solution was keep away from light and stored to 4° C. Then, mice were anesthetized using 0.1 ml of ketamine/xylazine solution per 10 g of body weight by intraperitoneal injection.

Sciatic Nerve Set Up Under Multiphoton Microscope

First injected mouse was anesthetized with 5% of isoflurane a 1.5% of oxygen into the anesthesia system box (World Precision Instruments, Ref. EZ-B800) for 5 minutes. Anesthesia controls were realized[8]. Then, mouse was placed in anesthesia mask and the incision area was shaved and cleaned with betadine and ethanol 70% solution. Incision was realized using a scalpel and the skin was retracted using forceps in order to expose the gluteus superficialis and biceps femoris muscles. Next, the connective tissue that connects both muscles was cut and the sciatic nerve was gently lifted out using a spatula. A flexible bridge was slide below sciatic nerve and it was placed into a plastic first pool fixed to the bridge. Mouse was placed under the multiphoton microscope, the bridge was fixed using magnetic brackets to avoid physiological movement and mouse legs were fixed using clippers. Microscope dark box temperature is controlled to 37° C. during all time-lapse imaging. Finally, a second pool was fixed to the first pool using a drop of agarose low melting 3% (Promega, Ref. V2111) in Leibovitz's L15 medium (Gibco Life Technologies) and filled with deionized water to immerse the objectives 20× or 63× (Carl Zeiss Microscopy).

Multiphoton Image Acquisition

All time-lapse images were obtained with a multiphoton microscope Zeiss LSM 7 MP OPO. Mitochondria motility images were acquired by time-lapse recording of one image every five minutes during five hours at 920 nm. GCaMP2 and SypHer probe images were acquired by time-lapse recording of one image every fifteen minutes during five hours at 985 nm. Images were acquired to constant 1% of laser intensity to 100 msec of acquisition time with 512×512 resolution and 10 images of z-stack of 20 µm. Images were saved in Zeiss .czi format and processed using Image J program. For further details see Gonzalez et al., 201X[8]

Electron Microscopy and Morphometry

Sciatic nerves of 20 and 28 weeks old diabetic mice or 16 and 24 weeks old CMT1A rats treated with TRO19622 drug or PBS were fixed for 20 min in situ with 4% PFA and 2.5% glutaraldehyde, in 0.1 M phosphate buffer (pH7.3). Then nerves were removed and postfixed overnight in the same buffer.

After washing 30 min in 0.2M PBS phosphate buffer, the nerves were incubated with 2% osmic acid in 0.1M phosphate buffer for 90 minutes at room temperature. Then, samples were washed in 0.2M PBS phosphate buffer, dehydrated using ethanol gradient solutions and embedded in epoxy resin. For electron microscopy of sciatic nerves, ultrathin (70 nm) cross-sections were cut and stained with 1% uranylacetate solution and lead-citrate and analyzed using a HITACHI H7100 electron microscope at the 'Centre des Resources en Imagerie Cellulaire' (CRIC) (for further details see Cotter et al., 2010[9]). Semi-thin cross-sections (0.7 µm) were cut using a microtome (Leica, RM 2155) with a diamond knife (Histo HI 4317, Diatome). Sections were stained with blue of toluidine and observed using light microscope. G-ratio was determined using GRatioCalculator plugin of Image J. At less 200 fibers per animal were analysed.

Electrophysiology

Standard electroneurography was performed before, during and after TRO 19622 drug treatment on CMT1A rats and diabetic mice that were anesthetized with 3% isoflurane. A pair of steel needle electrodes (AD Instruments, MLA1302, Oxford, UK) was placed subcutaneously along the nerve at sciatic notch (proximal stimulation). A second pair of electrodes was placed along the tibial nerve above the ankle (distal stimulation). Supramaximal square wave pulses lasting 10 ms and 1 mA for mice and 3.6 mA for rats were delivered using a PowerLab 26T (AD Instruments, Oxford, UK). Compound muscle action potential (CMAP) was recorded from the intrinsic foot muscles using steel electrodes. Both amplitudes and latencies of CMAP were determined. The distance between the two sites of stimulation was measured alongside the skin surface with fully extended legs, and nerve conduction velocities (NCVs) were calculated automatically from sciatic nerve latency measurements (for further details Fledrich et al., 2014[10]).

Behavioral Tests:

Rotarod Test

The rotating rod apparatus (Bioseb) was used to measure neuromuscular coordination and balance of male diabetic mice at 16 weeks and male and females CMT1A rats at 12 weeks during PBS or TRO19622 treatment. Mice and rats were first given a pretraining trial of two days to familiarize them with the rotating rod. For control and diabetic mice latency to fall was measured at fixed speed 10 rpm over a 180 s time as a cut-off. No acceleration testing was performed for mice. For control and CMT1A rats latency to fall and maximum rpm (revolutions per minute) were measured at accelerated speed. Rotating speed was successively increased from 4 to 40 rpm in 10 s intervals over 300 s time as a cut-off. Each animal underwent three trials a day. For each day, data were averaged for each animal (values from the three trials), normalized according to animal weight and then averaged for each treated group.

CatWalk Test

Detailed analysis of gait was performed on free-walking 16 weeks old diabetic mice and 12 weeks old CMT1A rats using the CatWalk method (CatWalk XT 10.5, Noldus Information Technology) during PBS or TRO19622 treatment. The runs were analyzed when the speed of crossing was constant and homogenous. At least three compliant runs were analyzed for each animal. Data were averaged per animal, normalized according to animal weight and then per treated group. The resulting data provided quantitative parameters and qualitative walking patterns.

Grip Test

Neuromuscular strength of diabetic mice and CMT rats was assessed in standardized grip strength tests for front, hind and all limbs. All limbs grip strength was measured by rat supporting on the metal grid and pulling the animal's tail toward a horizontal grid connected to a gauge. Front and hind limb grip strength were measured by supporting the forelimbs or hindlimbs respectively and pulling the animal's tail toward a horizontal T-bar connected to a gauge. The maximum force (measured in newtons) exerted onto the T-bar or grid before the animals lost grip was recorded, and the mean of 3 repeated measurements was calculated. All data were normalized according to animal weight.

Fluorescent Probes Validation

Mouse sciatic nerves expressing mito-GCaMP2 or mito-SypHer were isolated three weeks after AAV particles infection. Nerves were washed in PBS and incubated in Leibovitz's L15 medium (Gibco Life Technologies) for 3 hours at 37° C. in an atmosphere of 5% $CO_2$. Sciatic nerve infected with mito-SypHer probe was treated separately with sodium azide 3 mM solution (Sigma-Aldrich, Ref. S2002) or with ammonium chloride 30 mM solution (Sigma-Aldrich, Ref. A4514) for 5 minutes. Sciatic nerve infected with mito-GCaMP2 as treated separately with EDTA 1 mM solution (Sigma-Aldrich, Ref. ED255) or calcium chloride 100 µM solution (Sigma-Aldrich, Ref. S3014) and saponine 20 µg/µl solution (Sigma-Aldrich, Ref. S4521) for 5 minutes. Mito-SypHer and mito-GCaMP2 probe intensities were quantified at 985 nm using multiphoton microscope.

Genotype Analysis

Homozygous diabetic mice for leptin mutant (BKS(D)-Lepr$^{db+/+}$/JOrlRj) and their heterozygous controls (BKS(D)-Lepr$^{db+/-}$/JOrlRj) in a C57BL/KS-J background were purchased from Janvier Labs (Le Genest St. Isle, France). The generation of Pmp22 transgenic CMT1A rats has been previously described in Sereda et al., 1996[11]. Routine genotyping was performed by polymerase chain reaction (PCR), using genomic DNA from tail biopsies and the transgene-specific primers under standard conditions.

Data and Statistical Analysis

The data show the mean±SEM. Statistical significances were determined using a two-tailed Student's t test and one-way ANOVA followed by a Dunnett's multiple comparison post hoc test. Significance was set at * and #P<0.05,  and ##P<0.01, or * and ###P<0.001. ns represents non-significant differences (p>0.05). n represents the number of independent experiments.

Results

Characterization of Mitochondrial Physiology During Schwann Cell Demyelination

To characterize mitochondria physiology during the demyelination process we combined two in vivo methods. We used the nerve crush model to reliably induce demyelination in the mouse sciatic nerve and a viral approach[19] allowing the expression of different fluorescent probes selectively into mitochondria of myelinating Schwann cells (mSC) in mouse sciatic nerve. Three weeks after virus injection and probes expression, mice were anesthetized, their sciatic nerve exposed and placed under a multiphoton microscope allowing mSC mitochondria imaging in physiological conditions as described previously[20]. Then the nerve was carefully crushed around 5 mm upstream of the imaging area and changes occurring in mSC mitochondria downstream of the crush were recorded using the virally-delivered fluorescent probe. As a start we expressed the fluorescent probe mito-GCaMP2 allowing mitochondrial calcium measure in real time[21]. So we were able to follow mitochondrial calcium content in mSC before and after nerve crush and compare it to non-crushed controls. We observed a strong decrease of mitochondrial calcium starting one hour after crush whereas calcium concentrations did not change in control conditions. This loss of calcium was transitory as calcium levels were back to normal 1 hour later (2 hours after crush). Curiously 2 hours later (4 hours after crush) this basal level of calcium increased progressively to reach 133% at the end of the experiments (5 hours after crush), suggesting that mitochondria calcium homeostasis was altered on the long term after crush. We then expressed this probe in the mSC cytoplasm and we observed a transitory increase of cytoplasmic calcium paralleling the transitory loss of mitochondrial calcium, indicating that mitochondria released their calcium in the cytoplasm. No change was recorded on the long term in cytoplasmic calcium, suggesting that the long term hypercalcemia in mitochondria was specific to mitochondria.

To go further we investigated the mitochondrial pH in control and demyelinating SC using a virus expressing the mitochondria-targeted pH sensitive probe mito-SypHer[22,23]. We observed a significant increase of mitochondrial matrix pH two hours after nerve injury whereas non-demyelinating SC (control) maintained a stable mitochondrial pH over the time-lapse imaging. This increase in pH was permanent and reached a plateau that was maintained until the end of the experiment, suggesting that mitochondria activity definitely changed 2 hours after nerve injury.

Because mitochondrial shape and motility appear to be essential for mitochondrial functions[24], we also investigated mitochondrial dynamics and morphology in demyelinating SC using a virus expressing the fluorescent protein mito-dsRed2. While in non-crushed control nerves no change mitochondrial dynamics, fusion-fusion ratio and size, we observed a progressive decrease of mitochondria motility 1 hour after crush parallel to the mitochondrial calcium release. However this was not correlated with variation in fusion and fission ratio and mitochondrial size, suggesting that the molecular mechanisms allowing mitochondria movements were altered but not the ones responsible for fusion and fission events.

To summarize, nerve injury generated a fast signaling in mSC mitochondria starting around one hour after crush by the release of mitochondrial calcium in the cytoplasm; simultaneously mitochondria movements slowed down. One hour later when mitochondrial calcium came back to normal conditions, mitochondrial pH progressively increased to reach a plateau and then mitochondria started the accumulation of calcium. All together this succession of events suggests that one of the earliest responses of mSC to nerve injury is a pulse of mitochondrial calcium in the cytoplasm followed by a profound change in mitochondria physiology.

VDAC1 is the Responsible of Mitochondrial Changes in Schwann Cell after Nerve Crush To go further we investigated the molecular mechanism that mediates the release of mitochondria calcium after crush. VDAC1, Voltage-Dependent Anion-selective Channel 1, is a porin ion channel located on the outer mitochondrial membrane[25,26] and strongly expressed in mSC mitochondria[27]. VDAC1 is known as a major regulator of mitochondrial calcium release playing an essential role in cell signaling, apoptosis and dedifferentiation[25]. In order to test whether VDAC1 plays a role in the mitochondrial calcium release, two small inhibitory RNAs effective against VDAC1 expression were selected and cloned in viral vectors together with fluorescent probes. These viral vectors were produced, purified and injected in the sciatic nerve of mice in order to silence VDAC1 expression in mSC in vivo. Vectors expressing dsRed2 shRNA (for GFP-based probes) or GFP shRNA (for mito-dsRed2 probe) together with fluorescent probes were used as control. We first confirmed that both VDAC1 shRNAs were able to significantly reduce the channel expression in infected cells. This reduced expression did not change mitochondrial or cytoplasmic calcium, mitochondrial motility or pH in basal conditions. However after nerve crush, shRNA2 significantly reduced and shRNA3 completely inhibited mitochondrial calcium release in mSC, showing that VDAC1 mediates the release of mitochondrial calcium. As expected, control shRNA did not modify calcium release behavior after nerve injury. A similar effect was observed when nerves expressing mito-GCaMP2 were treated before crush with TRO19622, a reported selective ligand of mitochondrial VDAC1[28], showing that this drug is able to block calcium release from mitochondria. We also treated non-crushed nerves expressing mito-GCaMP2 with methyl jasmonate (MJ), a drug that increase VDAC permeability[29]. We observed that mSC mitochondria calcium concentration sharply decreased two hours after MJ injections compared to vehicle injection, showing that VDAC1 opening is sufficient to release mitochondrial calcium even in absence of crush injury. Taken together these data indicate that VDAC1 is necessary and sufficient to release mitochondrial calcium in mSC after nerve crush.

Because VDAC also participate to the formation of the mPTP, mitochondrial Permeability Transition Pore, we selectively blocked mPTP activity after crush using cyclosporin A[30]. We did not observe any change in calcium release in these conditions, confirming that VDAC1 is sufficient for mitochondrial calcium release during demyelination.

We also infected mSC with viral vectors expressing VDAC1 shRNAs and cytoplasmic GCaMP2 to observe the presence of mitochondrial calcium in the cytoplasm. VDAC1 shRNA3 strongly reduced the presence of cytoplasmic calcium in mSC after crush whereas the reduction was more modest with VDAC1 shRNA2 and absent with control shRNA. Consistently TRO19622 also induced a strong reduction of the calcium presence in the cytoplasm while MJ increased it. So, together these data show that mitochondrial calcium release via VDAC1 opening correlates with the presence of a calcium peak in cytoplasm. We observed also that while VDAC shRNA3 and TRO19622 completely abolished calcium release from mitochondria, they did not have the same radical effect on the presence of calcium in the cytoplasm, suggesting that a small part (13%) of the calcium appearing in the cytoplasm after nerve crush was from a non-mitochondrial origin.

When AAV were used to express each VDAC1 shRNA together with the mito-SypHer probe we observed that the pH increase in mitochondria after crush was significantly reduced in absence of VDAC1. Similar results were obtained when VDAC1 was blocked using TRO19622 drug. Conversely we observed an increase of mitochondrial pH when non-crushed nerves expressing mito-SypHer were treated with MJ. In addition VDAC1 shRNA2 and VDAC1 shRNA3 significantly prevented the loss of mitochondrial motility after nerve crush whereas shRNA control did not modify mitochondrial behavior 5 hours after nerve injury. Similar results were obtained when nerves were treated with TRO19622 30 minutes before crush. Finally, even without crush the treatment with MJ decreased mitochondrial motility whereas vehicle injections did not change it. Together these data show that the increase of mitochondrial pH and the decrease of mitochondrial motility during demyelination are due to the release of mitochondrial calcium through VDAC1 activity.

It is worth noting however that neither VDACsh3 nor TRO19622 totally abrogate the changes induced by nerve crush in mitochondrial pH (12%) and mitochondrial motility (20%). This suggests that the non-mitochondrial part of the calcium occurring in the cytoplasm after nerve crush partially contributes to these mitochondrial effects.

The Release of Mitochondrial Calcium Via VDAC1 Induces Schwann Cell Demyelination As nerve crush is known to generate SC demyelination, we reasoned that the release of mitochondrial calcium could activate a pathway leading to demyelination. These demyelination pathways are known: the classical ERK1/2[31], p38 and JNK[32] pathways. All of them increase the phosphorylation of c-jun, a transcription factor activated during demyelination[33]. To investigate the signaling pathways induced by mitochondrial calcium release, sciatic nerves were treated with vehicle or TRO19622 before crush or with MJ without crush and phosphorylation-activated pathways were determined by western blot 4 hours or 12 hours after nerve crush or MJ treatment. As expected an increase in phospho-ERK1/2, phospho-p38, phospho-JNK and phospho-c-jun was observed at 4 and 12 hours after sciatic nerves injury and vehicle. At both time points this effect was strongly reduced when nerves were treated with TRO19622 before crush. When nerves were not crushed but treated with MJ instead we observed also a significant increase in all phosphorylation-activated pathways and in phospho-c-jun either at 4 or 12 hours after treatment. Together these data indicate that the mitochondrial calcium release induced in SC by nerve crush generates the phospho-activation of all signaling pathways implicated in demyelination and leads to c-jun activation and importantly TRO19622 prevents these effects. Mitochondrial calcium release has been involved in other cell type in cell death and apoptosis[25,37]. While it is known that SC demyelination is not due to cell death but to a dedifferentiation process, we nevertheless checked mitochondria-related cell death factors in crushed or MJ treated nerves. Neither phospho-bcl2 nor cleaved caspase-3 levels were increased after nerve crush or MJ treatment, indicating that mitochondrial calcium release does not induce cell death.

To go further we also selectively silenced VDAC1 in mSC and measured the expression level of nuclear phospho-c-jun by immunohistochemistry after nerve crush. As expected nerve crush induced a strong expression of activated phospho-c-jun in the nucleus of demyelinating SC and the expression of control shRNA did not change this effect. However a strong reduction of phospho-c-jun was observed when VDAC1 was partially or completely silenced using AAV expressing VDAC shRNAs 2 or 3 respectively. The basal levels of c-jun were not altered by VDAC1 silencing. Consistently, nerves treated with MJ showed a robust increase in nuclear phospho-c-jun and the treatment with TRO19622 30 minutes prior crush strongly reduced phospho-c-jun activation in mSC. Together these data show that mitochondrial calcium release induced by nerve crush or MJ activates phospho-c-jun in the mSC nucleus and TRO19622 treatment prevents this effect.

Finally we also investigated the demyelination using typical defects induced in the cellular morphology of mSC. Nerves expressing control or VDAC1 shRNAs were crushed to induce demyelination and four days later, when demyelination is maximal, we analyzed the morphology of VDAC1-silenced mSC using confocal microscopy as described previously[19]. mSC display long homogenous noodle-like morphology with a regular diameter but during demyelination, they acquire a heterogeneous morphology often alternating large structures (myelin ovoids) with thin processes and their extremities split in fine extensions. After nerve crush more than 90% of the SC expressing control shRNA had a demyelinating phenotype compared to less than 10% without crush. When VDAC1 was selectively silenced with shRNA 2 or 3, we observed a significant increase in the number of myelinating cell remaining after crush, suggesting that blocking mitochondrial calcium release via VDAC1 silencing prevented demyelination. Moreover, when mice were treated with TRO19622 (intraperitoneal or intranerve injections) before and daily after nerve injury, the number of demyelinating cells was strongly reduced. Oppositely VDAC1 opening in non-crushed sciatic nerves using MJ induced a significant increase in the number of demyelinating cells. So these data confirm that mitochondrial calcium release via VDAC induces SC demyelination and TRO19622 prevents this demyelination by VDAC1 activity inhibition.

Mitochondrial Physiology and VDAC1 Activity are Altered in Schwann Cells of Diabetic Mice Diabetes is deeply linked to mitochondrial dysfunctions[35,36]. One of the major comorbidity associated with diabetes is a peripheral neuropathy characterized by a chronic demyelination. Indeed depending of the studies, up to 23.5% of diabetic patients have a peripheral neuropathy and this rise to 50% in aged diabetic people[4,6]. However the causes of these peripheral nerve defects are unknown. We hypothesized that defects in mSC mitochondrial calcium storage and/or release could be a cause of the disease. To test this hypothesis, we expressed our fluorescent probes in mSC of diabetic db/db mice and control +/db mice. We first observed that the relative calcium concentration in mSC mitochondria of diabetic mice was 2.1 times lower than in control mice at basal conditions. Oppositely, the relative cytoplasmic calcium was higher. In addition mitochondrial pH increased and mitochondrial motility decreased. To go further we then induced demyelination by crushing nerve and followed calcium release from mitochondria. When initial levels were normalized, we observed that mSC mitochondria in diabetic and control mice released their calcium at the same time and with a similar kinetic of activation. However mitochondria of diabetic mSC remained in low calcium for much longer time than controls, suggesting that the release of the calcium could not be stopped or the refill of mitochondria with calcium was impaired. The first hypothesis was confirmed by the cytoplasmic calcium probe as we observed that calcium appeared in the cytoplasm of diabetic mSC at a similar kinetic as control but remained high for a much longer time. This defective control of calcium release by mitochondria suggested that calcium leaks out of diabetic mSC mitochondria. This may explain why the relative calcium amount in diabetic mSC is higher in the cytoplasm and lower in mitochondria versus controls. The consequences of this calcium leak were first, a permanent increase in mitochondrial pH and therefore a reduced pH response after nerve crush and second, reduced mitochondrial movements close to basal levels, which limited the drop after nerve injury. However we also noted that neither changes in fusion and fission ratio nor mitochondrial size differences were found between diabetic and control mice along 5 hours after crush, showing that these mechanisms were not affected in diabetic mSC.

So we conclude that the physiology of mitochondria is strongly affected in mSC of diabetic mice. Calcium appears to leak out of mitochondria which results in altered levels of cytoplasmic and mitochondrial calcium, increased mitochondrial pH and reduced mitochondrial movements.

Inhibiting Mitochondrial Calcium Release in Schwann Cells Prevents Demyelination In Vivo Looking at VDAC1 expression of in the sciatic nerve of diabetic mice we found no difference with control mice in basal conditions. In order to determine whether VDAC1 is involved in diabetic mSC mitochondrial anomalies, we first expressed VDAC1 shRNAs together with fluorescent mitoprobes in mSC of diabetic mice. After three weeks of VDAC1 silencing we observed a significant increase in relative mitochondrial calcium concentration and a proportional decrease in cytoplasmic calcium. Moreover similar changes were obtained on both parameters when diabetic mice were treated with IP injections of VDAC1 specific inhibitor, TRO19622, for four days, showing that VDAC1 is indeed responsible for the calcium leak in the cytoplasm. Finally, reducing mitochondrial calcium leak by VDAC1 silencing or TRO19622 inhibition significantly reduced mitochondrial pH and increased mitochondrial motility, which is consistent with a reduced mitochondrial calcium release in cytoplasm. So silencing VDAC1 expression or inhibiting its function can prevent the consequences of calcium leakage in diabetic mSC.

Diabetes peripheral neuropathy in humans is characterized by a chronic demyelination. In mouse models of diabetes peripheral nerve defects (thinner myelin, reduced nerve conduction velocity, motor impairment) and activation of the demyelination signaling can be detected at early adult age[37,38]. However demyelination is not significant before 1-1.5 years and therefore overlaps with peripheral nerve defects due to ageing[39-41]. So we choose not to focus on demyelination itself but on early peripheral nerve defects in db/db diabetic mice[37,38]. Firstly, we found high expression levels of nuclear phospho-c-jun in diabetic mSC and silencing VDAC1 expression strongly reduced these levels. Similar results were obtained when mice were treated with TRO19622 for 15 or 30 days, showing that VDAC1 silencing or inhibition prevents demyelination signaling pathways activation in diabetic mice.

To go further 16-weeks-old diabetic and control mice were treated daily with vehicle or TRO19622 for one month. One day and two months after drug treatment, myelin was evaluated in the sciatic nerve using toluidine blue staining and transmission electron microscopy (TEM) to measure the g-ratio (axon diameter on total myelinated fiber diameter). We observed a significant decrease in the g-ratio of diabetic mice treated with TRO19622 compared to mice treated with vehicle. No differences were found in axon number and diameter, indicating that VDAC1 inhibition allows for a thicker myelin similar to the myelin of non-diabetic mice.

Figure 1B:
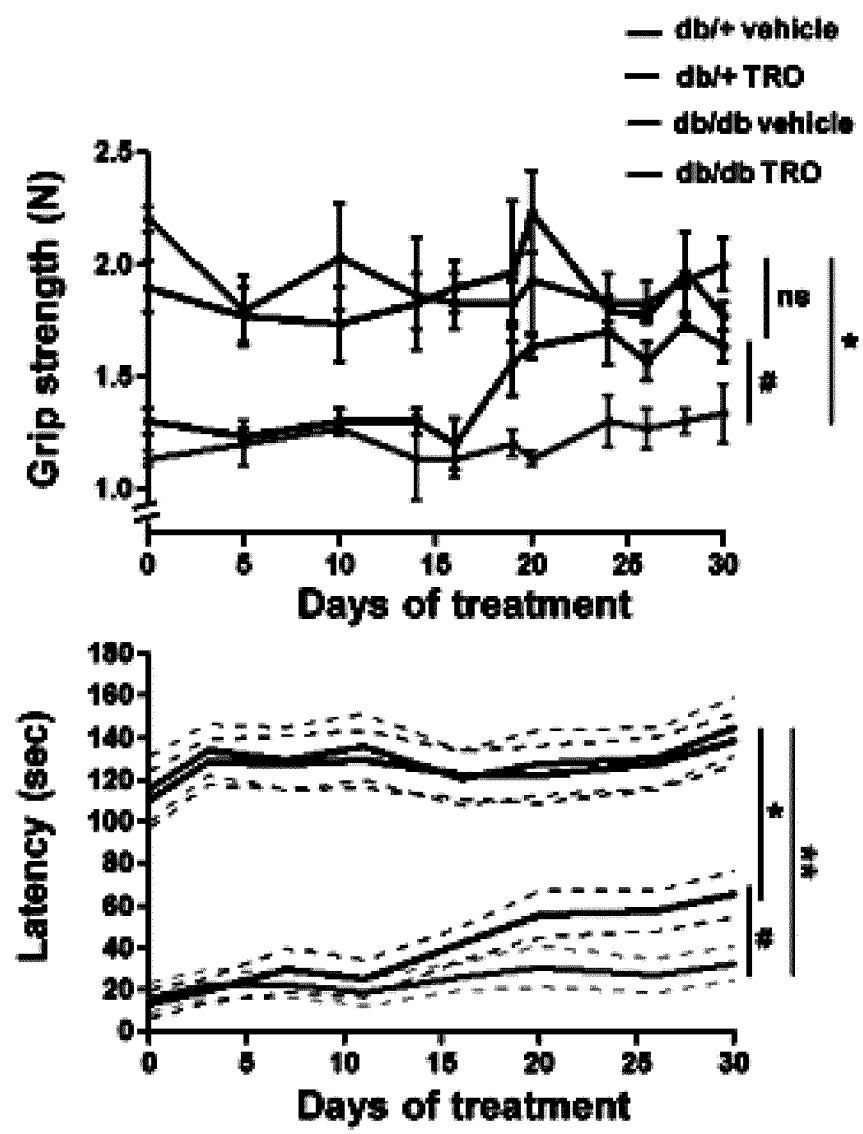

As previously reported[37,38], we observed a reduction of the nerve conduction velocity in db/db diabetic mice with no change in the amplitude of the compound of action potentials (CMAP). After 30 days of TRO19622 treatment this nerve conduction velocity significantly increased to reach control mice velocity (FIG. 1A bottom panel) still without change in CMAP amplitude (FIG. 1A top panel).

Finally, although the obesity of db/db diabetic mice hinders functional motor tests, we evaluated their neuromuscular performances during drug treatment using rotarod, grip and Catwalk tests. A significant increase in rotarod latency and grip strength were observed 20 days after TRO19622 treatment in diabetic mice (FIG. 1B) but no change was found in Catwalk test parameters. Rotarod and grip strength recoveries were not due to a reduced weight as no change in mice weight was observed during treatment. We conclude that the inhibition of VDAC1 function with TRO19622 prevents the activation of demyelination signaling in mSC of diabetic mice and this result in an improvement of the myelin thickness, the nerve conduction and the motor performances.

While demyelinating diabetes peripheral neuropathy is a commonly acquired disease, demyelination is also the characteristic feature of a large number of inherited diseases called Charcot-Marie-Tooth diseases (CMT). We therefore sought to test whether the inhibition of VDAC1 function could prevent demyelination in these diseases. We choose CMT1A rat strain[42] as this is arguably the most representative animal model of Charcot-Marie-Tooth disease, mimicking CMT1A the most prevalent CMT in humans[10]. Twelve weeks old CMT1A rats were daily treated with TRO19622 for 15 or 30 days and one day or two months after treatment, we analyzed MAPK demyelination pathways by western blot. We observed a strong activation of phospho-ERK1/2, phospho-p38, phospho-JNK and phospho-c-jun in basal conditions as previously published[43,44] but after 15 and 30 days of TRO19622 treatment we showed a significant down-regulation of these pathways. However, these effects disappeared two months after treatment. Then we analyzed phospho-c-jun activation in mSC using immunohistochemistry. TRO19622 treatment strongly reduced phospho-c-jun amount in the mSC nucleus of CMT1A rats compared to vehicle, suggesting that inhibition of VDAC1 function prevents activation of demyelination pathways in mSC of CMT1A rats. Next, we measured Schwann cell demyelination and g-ratio by toluidine blue staining on semi-thin sciatic nerve sections and on thin sections using electron microscopy. We observed a reduction of the number of demyelinated fibers and a significant increase in the g-ratio of myelinated fibers in TRO19622 treated rats. Both number and diameter of axons in the nerve were also increased. Taking together this indicated that inhibiting VDAC1 in diseased animals halted demyelination, restored correct myelin thickness and prevented axonal loss.

In parallel we analyzed nerve conduction in CMT1A rats daily treated with TRO19622 for one month and we observed a significant increase of CMAP amplitude and of nerve condition velocity suggesting that improvement of myelination and preservation of axons following VDAC1 inhibition restore the nerve function in CMT1A rats.

Figure 2A:
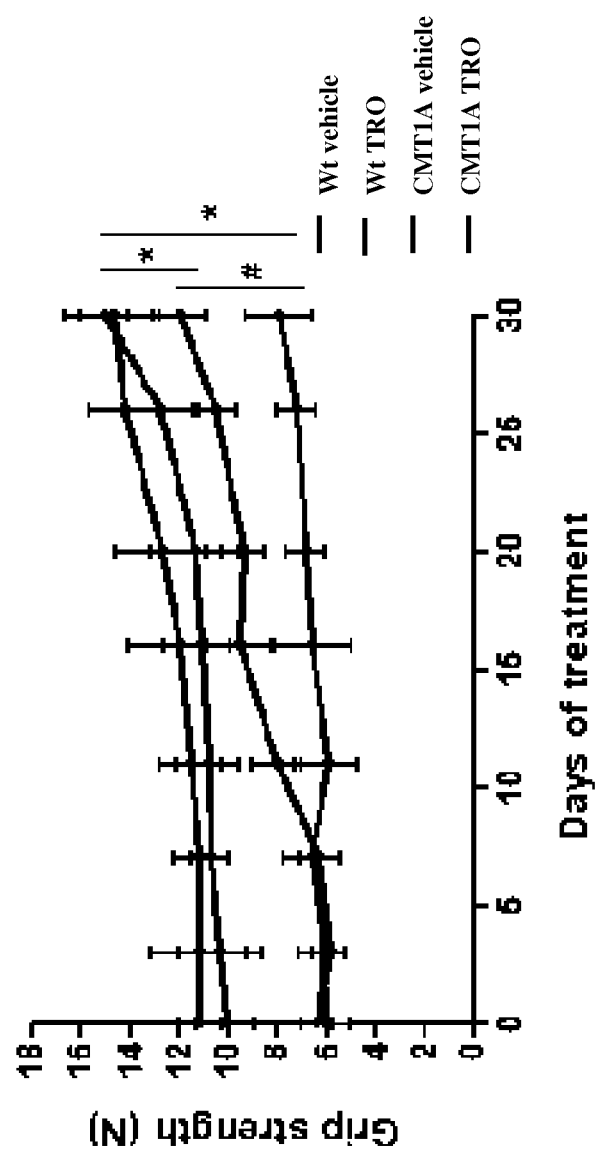
Figure 2B:
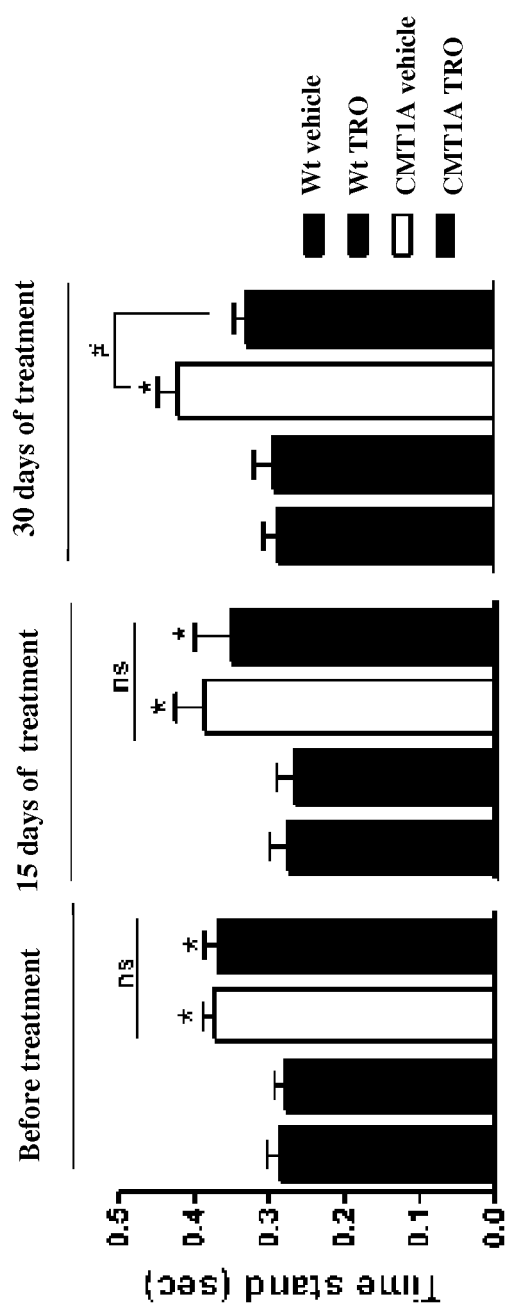
Figure 2C:
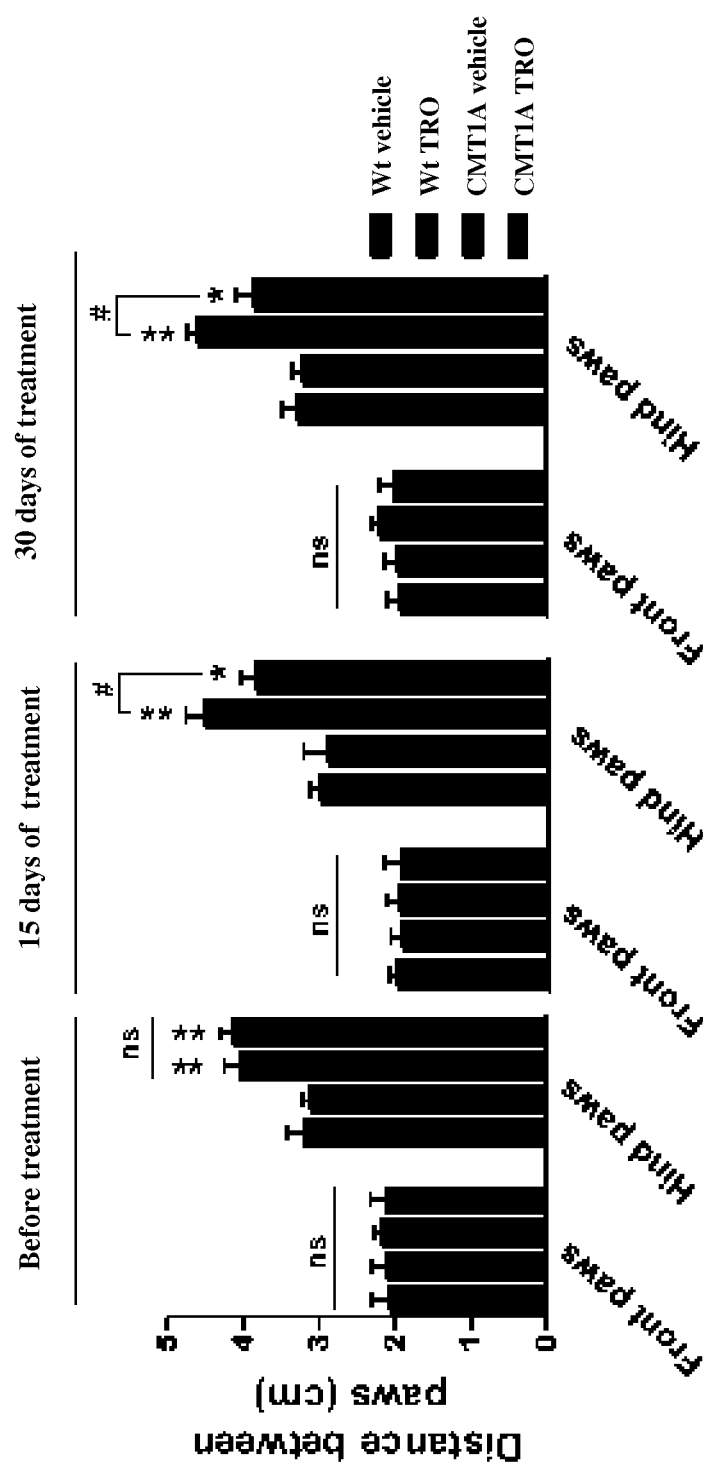
Figure 2D:
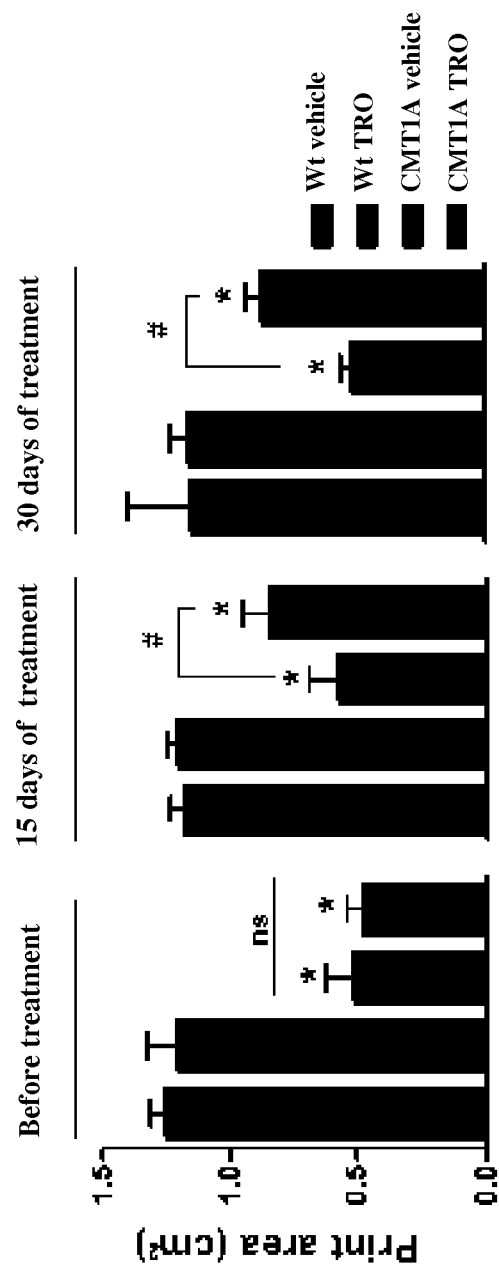

Finally, we studied the neuromuscular performance of CMT1A and control rats using behavioral motor tests. A significant increase of the latency on accelerating rotarod and of grip strength (FIG. 2A) were observed in diseased animals treated with TRO19622 for one month. Moreover, using catwalk test we observed a decrease of paw time stand (FIG. 2B), hind paw distance (FIG. 2C) and an increase of paw print area (FIG. 2D). All these changes showed a functional recovery of the motor performances of the diseased animals. This recovery was not due to change in the body mass as rats did not lose weight during treatment. However the effects of TRO19622 on demyelination, g-ratio and behavioral motor tests did not last and disappeared 2 month after stopping the treatment. Taken together, these data show that the inhibition of VDAC1 function with TRO19622 prevents the activation of demyelination pathways, halts demyelination, improves myelination, preserves axons and significantly increase nerve conduction and neuromuscular performances in CMT1A rats. Therefore inhibiting mitochondrial calcium release through VDAC1 opens a major avenue toward the treatment of human CMT1A.

Discussion:

While demyelinating peripheral nerve diseases include a large spectrum of disabling acquired and inherited diseases, mechanisms of mSC demyelination remain elusive. Peripheral nerve demyelination does not result from cell death but from mSC dedifferentiation. So demyelination is a cellular program in which the mSC enters upon specific signals such as axonal injury in a trauma. These triggering signals are transduced in the cell and drive the activation of MAPK demyelination pathways (p-ERK1/2, p-P38 and p-JNK activation) followed by the recruitment of phosphorylated c-jun in the nucleus. Here we describe an earlier step, the release of mitochondrial calcium and changes in mitochondria physiology.

Using a viral approach to express fluorescent probes in mitochondria of mSC in the sciatic nerve of living mice and a multiphoton microscope for time-lapse live imaging, we show that the release of mitochondrial calcium occurs as soon as one hour after inducing demyelination by nerve injury. This release is followed, in this specific order, by a burst of calcium in the cytoplasm, the slowing of mitochondrial movements, the increase of mitochondrial pH and mitochondrial hypercalcemia. Using silencing, activation/inhibition with drugs, we show that VDAC1 is responsible for the release of mitochondrial calcium in the cytoplasm. This pulse of mitochondrial calcium through VDAC1 activates the known demyelination pathways ERK1/2, p38 and JNK. This leads to the phosphorylation of c-jun in the nucleus, which characterizes the demyelination program in mSC[33]. However several other unclear cellular processes are also engaged and this will result in the collapse of the cell structure, the breakdown of the myelin[45] and the recruitment of macrophages to help to clear myelin debris[46]. Once demyelination is completed, around 5 days after crush of sciatic nerve, then dedifferentiated SC will be able to start a new program and remyelinate axons.

The release of calcium by mitochondria is the earliest step recorded after nerve injury and our data indicate that this step is necessary and sufficient for triggering the demyelination program. How this burst of mitochondrial calcium through VDAC1 channels activates ERK1/2, p38 and JNK pathways is not clear. However mitochondrial calcium release is an essential cell signaling triggering death and differentiation[34, 47]. Moreover cytoplasmic calcium stimulates Erk1/2[48] and JNK[49] activity. Several studies also reported an association of Erk1/2, p38 and JNK and of their direct activators such as Raf, Sab, and MKK4 with mitochondria[50]. So it is likely that mitochondrial calcium release in the cytoplasm directly activates MAPK demyelination pathways and these cascades pathways propagate the demyelination signal all over the cell. Nevertheless other mechanisms cannot be excluded such as a production of reactive oxygen species (ROS) in calcium-activated mitochondria to stimulate Erk1/2[51], p38[52] and JNK[53] pathways. But we did not detect any production of these compounds using a ROS-specific fluorescent probe[54] (RoGFP, data not shown). Whatever is the precise mechanism this mitochondrial signaling after nerve injury never reached the cell death level as cell-death related pathways such as caspase 3 and Bcl2 were not activated. Mitochondrial signaling is therefore able to generate a differentiation process instead of cell death, as previously reported in myoblast[55].

VDAC has numerous binding partners that controls its permeance and in particular hexokinase (HK). HK binding to VDAC reduces the permeability of the pore notably to calcium[56]. In Schwann cells methyl jasmonate, a compound that uncouples HK from VDAC[29], induced mitochondrial calcium release and demyelination showing that HK is essential to control demyelination. Intriguingly mutations in HK gene are responsible for demyelinating CMT4G[57], suggesting that an increased permeability of VDAC to calcium is the cause of the disease. On the opposite we show that TRO19622, a compound that binds to VDAC[28], blocks mitochondrial calcium release through VDAC preventing demyelination.

Mitochondrial calcium release through VDAC has other consequences that may contribute to the demyelination program too. First the slowdown of mitochondrial motility we observed after nerve crush is likely to be due to the increase of cytoplasmic calcium around mitochondria. Indeed calcium alters the activity of molecular motors that mediate mitochondrial movements in the cell[58]. Second mitochondrial pH is linked to cytoplasmic calcium concentration[22] so when mitochondria release calcium their pH changes. However while hypocalcemia is transitory pH changes on the long term (at least for 5 hours) suggesting that mitochondrial respiratory activity is increased[59]. As ATP controls the uptake of calcium from the endoplasmic reticulum[60] (ER), the mitochondrial hypercalcemia occurring 4 hours after nerve crush reflects also an increase in respiratory activity. Taken together this suggests that mitochondrial calcium release after nerve crush profoundly changes mitochondria physiology in mSC making them more active. How mitochondrial activity and metabolism changes participate to the demyelination program is a very interesting open question.

Peripheral demyelinating neuropathy is a major complication of diabetes and, while the pathomechanism of the disease is unknown, diabetic neuropathy has been related to mitochondrial stress and defects[17, 18]. For these reasons, we investigated whether mitochondrial physiology was altered in mSC before and after nerve injury in a diabetic mouse model[42, 43] This model, db/db mice mutated on the leptin receptor, develops hyperphagic obesity and nonketotic diabetes similar to non-insulin dependent diabetes mellitus in humans[61]. Diabetes and systemic metabolic alterations induced major changes in mitochondria of mSC: basal levels of calcium decreased in mitochondria matrix and increased in the mSC cytoplasm. As VDAC1 silencing and inhibition prevented these changes it suggested that mitochondrial calcium could leak through VDAC1. The analysis of mitochondrial calcium release and appearance in the cytoplasm after nerve injury showed a slowing of VDAC1 closure kinetic. So the channel, or its regulation such as by hexokinase, is altered in diabetic conditions and does not close properly. This is likely to be the cause of the calcium leak observed at basal conditions in mSC of diabetic mice. This higher amount of mitochondrial calcium signaling constitutively stimulates MAPK demyelination pathways and increases nuclear phospho-c-jun. So mSC of diabetic mice are primed for demyelination. Interestingly a calcium leak has also been characterized through mutant ryanodine receptors RyR2 in ER[62]. Calcium flowing through these leaky channels is responsible for mitochondrial dysfunction, ER stress and glucose intolerance, suggesting that impaired control of calcium release from the ER or from mitochondria has dramatic effect on cell physiology.

Human diabetic peripheral neuropathy is characterized by demyelinating features. Similar demyelination is seen in diabetic dogs and cats[63]. However demyelination is not seen in rodent models of diabetes except at late ages[37, 38, 64] This discrepancy may be due to difference between species mSC physiology but another explanation may be that diabetic peripheral neuropathy is a chronic disease and demyelination requires time to be primed and then completed. As the life of rodent is short this demyelination may not occur before old ages while in long lived mammals such as humans, cats and dogs demyelination can occur. Despite this absence of demyelination diabetic db/db peripheral neuropathy is characterized by a reduction of myelin thickness, decrease of nerve conduction velocity and neuromuscular defects showing that peripheral nerve function is affected in these mice. We have shown that the TRO16922 inhibition of mitochondrial calcium release via VDAC1 in mSC steadily improve all these parameters in diabetic mice, suggesting that this mechanism constitutes a potential therapeutic target to treat demyelinating diabetic peripheral neuropathy. Indeed TRO16922 has been tested in clinical trial phase IIa on painful diabetic neuropathy but this trial stopped in January 2009 for unclear reasons.

Peripheral nerve demyelination has many causes from axonal degeneration as in nerve injury, metabolic alterations as in diabetes to chromosomal mutations as in CMT diseases. Such heterogeneity has hindered the search for a treatment for demyelinating peripheral neuropathies. Blocking mitochondrial calcium release prevented demyelination in a classical nerve crush injury but also in a diabetic demyelination, suggesting that the mitochondrial step toward demyelination is common to different pathologies. To confirm this we used another completely different model of demyelination, the CMT1A rats. CMT1A, the main CMT disease, results from a duplication of PMP22 gene[65]. How overexpression of PMP22 induces demyelination is unclear but one hypothesis is that too much unfolded PMP22 saturates the proteasome/autophagy system leading to cell stress[66]. In rat this disease is mimicked by the transgenic expression of human PMP22[42]. We showed that inhibition of VDAC1 by TRO16922 prevented the activation of MAPK demyelination pathways and the c-jun phosphorylation in the nucleus. Moreover the treatment restored a correct g-ratio and rescued axonal loss. Nerve conduction was largely improved and this resulted in better performances of the animals in functional tests. Taken together this shows that mitochondrial calcium release through VDAC1 is involved in PMP22-driven demyelination and it constitutes also a potential therapeutic target to treat CMT1A. So, while it would probably be difficult to generalize, we believe that this mitochondrial step is likely to be involved in most of demyelinating peripheral neuropathies.

We noted that the effects of VDAC1 inhibition with TRO19622 on MAPK activation, nerve structure and neuromuscular performance did not last 2 months after stopping the treatment both in diabetic mice and in CMT1A rats. This suggests that mitochondrial calcium release is constitutive in these chronic diseases and transiently inhibiting VDAC1 activity cannot provide a definitive issue. Nevertheless, as inhibition of VDAC1 through TRO19622 has been shown to be safe in humans[67], new drug design or existing drug improvement could be an attractive possibility to generate a treatment with long lasting benefit.

The activation of MAPK demyelination pathways had been shown already to occur during demyelination of different origins, but this could not be exploited properly as therapeutic use because there are already too many pathways to control at this stage. As mitochondrial calcium release occurs earlier and is the source of MAPK activation and all subsequent steps, it provides a unique target for the potential treatment of many demyelinating peripheral neuropathies.

REFERENCES

Throughout this application, various references describe the state of the art to which this invention pertains. The disclosures of these references are hereby incorporated by reference into the present disclosure.

1. Sherman, D. L. and Brophy, P. J., Mechanisms of axon ensheathment and myelin growth. Nat Rev Neurosci, 2005. 6(9): p. 683-90.
2. Nave, K. A., Myelination and support of axonal integrity by glia. Nature, 2010. 468(7321): p. 244-52.
3. Hughes, R. A., Peripheral neuropathy. Bmj, 2002. 324 (7335): p. 466-9.
4. Zochodne, D. W., Diabetic polyneuropathy: an update. Curr Opin Neurol. 2008. 21(5):527-33.
5. Khoa, Pham et al., Understanding the mechanisms of entrapment neuropathies. Review article. Neurosurg Focus. 2009. 26 (2):E7.
6. Feldman, E. L., Stevens, M. J. and Greene, D. A., Pathogenesis of diabetic neuropathy. Clin Neurosci, 1997. 4:365-370.
7. Brownlee, M., Vlassara, H. and Cerami, A., Trapped immunoglobulins on peripheral nerve myelin from patients with diabetes mellitus. Diabetes, 1986. 35:999-1003.
8. Greene, D. A., Sima, A. A., Stevens, M. J., Feldman, E. L., and Lattimer, S. A., Complications: neuropathy, pathogenetic considerations. Diabetes Care, 1992. 15:1902-1925.
9. Harati, Y., Diabetic peripheral neuropathies. Ann. Intern. Med., 1987. 107(4):546-59.
10. Skre, H., Genetic and clinical aspects of Charcot-Marie-Tooth's disease. Clin Genet. 1974. 6(2):98-118.
11. Berger, P., et al., Loss of phosphatase activity in myotubularin-related protein 2 is associated with Charcot-Marie-Tooth disease type 4B1. Hum Mol Genet, 2002. 11(13): p. 1569-79.
12. de Moura, M. B., dos Santos, L. S. and Van Houten, B., Mitochondrial dysfunction in neurodegenerative diseases and cancer. Environ Mol Mutagen, 2010. 51(5): p. 391-405.
13. Schroder, J. M., Neuropathy associated with mitochondrial disorders. Brain Pathol, 1993. 3(2): p. 177-90
14. Viader, A., et al., Schwann cell mitochondrial metabolism supports long-term axonal survival and peripheral nerve function. J Neurosci, 2011. 31(28): p. 10128-40.
15. Kalman, B., Lublin, F. D. and Alder, H., Impairment of central and peripheral myelin in mitochondrial diseases. Mult Scler, 1997. 2(6): p. 267-78.
16. Cornblath, D. R. and Hoke, A., Recent advances in HIV neuropathy. Curr Opin Neurol, 2006. 19(5): p. 446-50.
17. Kalichman, M. W., Powell, H. C. and Mizisin, A. P., Reactive, degenerative and proliferative Schwann cell responses in experimental galactose and human diabetic neuropathy. Acta Neuropathol, 1998. 95(1): p. 47-56.
18. Fernyhough, P., Roy Chowdhury, S. K. and Schmidt R. E., Mitochondrial stress and the pathogenesis of diabetic neuropathy. Expert Rev Endocrinol Metab, 2010. 5(1): p. 39-49.
19. Gonzalez, S., Fernando, R., Perrin-Tricaud, C., and Tricaud, N. In vivo introduction of transgenes into mouse sciatic nerve cells in situ using viral vectors. Nat. Prot., 2014. 9(5):1160-9.
20. Gonzalez, S, Fernando, R, Berthelot J., Perrin-Tricaud, C., et al., In vivo time-lapse imaging of mitochondria in healthy and diseased peripheral myelin sheath. Submitted to Mitochondrion 2015.
21. Chen, M. et al., Differential mitochondrial calcium responses in different cell types detected with a mitochondrial calcium fluorescent indicator, mito-GCaMP2. Acta Biochim Biophys Sin, 2011. 43: 822-830.
22. Poburko, D. et al., Dynamic Regulation of the Mitochondrial Proton Gradient during Cytosolic Calcium Elevations. J. Biol. Chem., 2011. 286:11672-11684.
23. Roma, L. et al., Dynamic measurements of mitochondrial hydrogen peroxide concentration and glutathione redox state in rat pancreatic β-cells using ratiometric 23. fluorescent proteins: confounding effects of pH with HyPer but not roGFP1. Biochem. J., 2012. 441, 971-978.
24. Palmer, C S et al., The regulation of mitochondrial morphology: Intricate mechanisms and dynamic machinery. Cell Signal, 2011. 23(10):1534-45.
25. Shoshan-Barmatz, V., and Gincel, D., The voltage-dependent anion channel: characterization, modulation, and role in mitochondrial function in cell life and death. Cell Biochem. Biophys, 2003. 39(3): 279-92.
26. Shoshan-Barmatz, V., and Ben-Hail, D. VDAC, a multi-functional mitochondrial protein as a pharmacological target. Mitochondrion, 2012. 12(1):24-34.
27. Ritchie, J. M. Voltage-gated cation and anion channels in mammalian Schwann cells and astrocytes. Physiol (Paris), 1987. 82(4):248-57.
28. Bordet, T., et al., Identification and Characterization of Cholest-4-en-3-one, Oxime (TRO19622), a Novel Drug Candidate for Amyotrophic Lateral Sclerosis. J Pharmacol Exp Ther, 2007. 322(2):709-20.
29. Goldin, N., et al., Methyl jasmonate binds to and detaches mitochondria-bound hexokinase. Oncogene, 2008. 27, 4636-4643.
30. Sharov, V. G., et al., Cyclosporine A Attenuates Mitochondrial Permeability Transition and Improves Mitochondrial Respiratory Function in Cardiomyocytes Isolated from Dogs With Heart Failure. J Mol Cell Cardiol, 2007. 42(1): 150-158.
31. Napoli, I., Noon, L. A., Ribeiro, S., et al., A central role for the ERK-signaling pathway in controlling Schwann cell plasticity and peripheral nerve regeneration in vivo. Neuron, 2012. 73(4):729-42
32. Lee, H. J., Shin, Y. K. and Park, H. T., Mitogen Activated Protein Kinase Family Proteins and c-jun Signaling in Injury-induced Schwann Cell Plasticity. Experimental Neurobiology, 2014. 23(2):130-137.
33. Parkinson, D. B., et al., c-Jun is a negative regulator of myelination. J Cell Biol, 2008. 181(4):625-637.
34. De Stefani, D et al., VDAC1 selectively transfers apoptotic $Ca^{2+}$ signals to mitochondria. Cell Death Differ., 2012. 19(2):267-73.
35. Kalichman, M. W., Powell, H. C., and Mizisin, A. P., Reactive, degenerative, and proliferative Schwann cell responses in experimental galactose and human diabetic neuropathy. Acta Neuropathol, 1998. 95(1): p. 47-56.
36. Fernyhough, P., Roy Chowdhury, S. K, and Schmidt, R. E., Mitochondrial stress and the pathogenesis of diabetic neuropathy. Expert Rev Endocrinol Metab, 2010. 5(1): p. 39-49.
37. Hamilton, R. T., et al., Elevated Protein Carbonylation, and Misfolding in Sciatic Nerve from db/db and Sod12/2 Mice: Plausible Link between Oxidative Stress and Demyelination. PLoS ONE, 2013. 8(6):e65725
38. Wang, L., et al., Phosphodiesterase-5 is a therapeutic target for peripheral neuropathy in diabetic mice. Neuroscience, 2011. 193:399-410
39. Robertson, D. M., and Sima, A. A., Diabetic neuropathy in the mutant mouse [C57BL/ks(db/db)]: a morphometric study. Diabetes, 1980. 29(1):60-7.
40. Sharma, A. K., et al., Peripheral nerve abnormalities in the diabetic mutant mouse. Diabetes, 1983. 32(12):1152-61.
41. Sassoli Fazan, V. P., Carvalho de Vasconcelos, C. A. et al., Diabetic peripheral neuropathies: A morphological overview. Int. J. Morphol. 2010. 28(1): 51-64.
42. Sereda, M., et al., A Transgenic Rat Model of Charcot-Marie-Tooth Disease. Neuron, 1996. 16, 1049-1060
43. Fledrich, R., et al., Soluble neuregulin-1 modulates disease pathogenesis in rodent models of Charcot-Marie-Tooth disease 1A. Nat Med. 2014. 20(9):1055-61.
44. Hutton, E. J., et al., c-Jun expression in human neuropathies: a pilot study. JPNS, 2011. 16:295-303.
45. Salzer, J. L. Switching myelination on and off. J Cell Biol, 2009. 19; 181(4):575-7.
46. Martini, R., Fischer, S., Lopez-Vales, R. and David, S. Interactions between Schwann cells and macrophages in injury and inherited demyelinating disease. Glia, 2008. 56(14):1566-77.
47. Rizzuto, R., De Stefani, D., Raffaello, A. and Mammucari, C Mitochondria as sensors and regulators of calcium signalling. Nat Rev Mol Cell Biol. 2012, 13(9):566-78.
48. Chuderland, D and Seger, R. Calcium regulates ERK signaling by modulating its protein-protein interactions. Commun Integr Biol. 2008, 1(1): 4-5.
49. Enslen, H, Tokumitsu, H, Stork, P J, Davis, R J, Soderling, T R. Regulation of mitogen-activated protein kinases by a calcium/calmodulin-dependent protein kinase cascade. Proc Natl Acad Sci USA. 1996, 93(20): 10803-8.
50. Javadov, S., Jang, S. and Agostini, B. Crosstalk between mitogen-activated protein kinases and mitochondria in cardiac diseases: therapeutic perspectives. Pharmacol Ther. 2014, 144(2):202-25
51. Schäfer, M, Schäfer, C, Ewald, N, Piper, H M and Noll, T. Role of redox signaling in the autonomous proliferative response of endothelial cells to hypoxia. Circ Res. 2003, 92(9): 1010-5.
52. Kulisz, A., Chen, N., Chandel, N. S., Shao, Z. and Schumacker, P. T. Mitochondrial ROS initiate phosphorylation of p38 MAP kinase during hypoxia in cardiomyocytes. Am J Physiol Lung Cell Mol Physiol. 2002 June; 282(6):L1324-9
53. Dougherty, C. J., Kubasiak, L. A., Frazier, D. P., Li, H., Xiong, W. C., Bishopric, N. H. and Webster, K. A. Mitochondrial signals initiate the activation of c-Jun N-terminal kinase (JNK) by hypoxia-reoxygenation. FASEB J. 2004, 18(10):1060-70.
54. Hanson, G. T., Aggeler, R., Oglesbee, D., Cannon, M., Capaldi, R A., Tsien, R, Y. and Remington, S. J. Investigating mitochondrial redox potential with redox-sensitive green fluorescent protein indicators. J Biol Chem, 2004. 279 (13): 13044-53.
55. Porter, G. A., Makuck, R. F. and Rivkees, S. A. Reduction in intracellular calcium levels inhibits myoblast differentiation. J Biol Chem. 2002, 277(32):28942-7.
56. Shoshan-Barmatz, V., Israelson, A., Brdiczka, D. and Sheu, S. S. The Voltage-Dependent Anion Channel (VDAC): Function in Intracellular Signalling, Cell Life and Cell Death. Current Pharm Design: 2006, 12, 2249-2270
57. Hantke, J., Chandler, D., King, R., et al., A mutation in an alternative untranslated exon of hexokinase 1 associated with hereditary motor and sensory neuropathy—Russe (HMSNR). Eur J Hum Genet. 2009,17(12):1606-14.
58. Yi, M., Weaver, D. and Hajnoczky, G. Control of mitochondrial motility and distribution by the calcium signal: a homeostatic circuit. J Cell Biol., 2004. 167(4): 661-72.
59. Santo-Domingo, J. and Demaurex, N., The renaissance of mitochondrial pH. J Gen Physiol, 2012. 139(6):415-23.
60. García-Sancho, J. The coupling of plasma membrane calcium entry to calcium uptake by endoplasmic reticulum and mitochondria. J Physiol. 2014, 592(Pt 2):261-8.

61. Chen, H., Charlat, O., Tartaglia, L. A., et al., Evidence that the diabetes gene encodes the leptin receptor: identification of a mutation in the leptin receptor gene in db/db mice. Cell. 1996, 84(3):491-5.
62. Santulli, G., Pagano, G., Sardu, C., Xie, W., Reiken, S., D'Ascia, S. L., et al., Calcium release channel RyR2 regulates insulin release and glucose homeostasis. J Clin Invest. 2015, 125(5):1968-78.
63. Mizisin, A. P., Nelson, R. W., Sturges, B. K., Vernau, K. M., et al., Comparable myelinated nerve pathology in feline and human diabetes mellitus. Acta Neuropathol. 2007, 113(4):431-42.
64. Zenker, J., Poirot, O., de Preux Charles, A. S., Arnaud, E., et al., Altered distribution of juxtaparanodal kv1.2 subunits mediates peripheral nerve hyperexcitability in type 2 diabetes mellitus. J Neurosci. 2012, 32(22):7493-8.
65. Lupski, J. R., de Oca-Luna, R. M., Slaugenhaupt, S., Pentao, L., et al., DNA duplication associated with Charcot-Marie-Tooth disease type 1A. Cell. 1991, 66(2):219-32.
66. Chittoor-Vinod, V. G., Lee, S., Judge, S. M. and Notterpek, L. Inducible HSP70 is critical in preventing the aggregation and enhancing the processing of PMP22. ASN Neuro. 2015, 7(1). pii: 1759091415569909.
67. Martin, L. J. Olesoxime, a cholesterol-like neuroprotectant for the potential treatment of amyotrophic lateral sclerosis. IDrugs. 2010, 13(8):568-80.

---

The invention claimed is:

1. A method of treating a peripheral demyelinating disease in a subject in need thereof comprising administering to the subject a therapeutically effective amount of an inhibitor of VDAC1 activity or expression in Schwann cells,
wherein said therapeutically effective amount is sufficient to inhibit VDAC1 activity or expression in said Schwann cells, and
wherein said peripheral demyelinating disease is selected from the group consisting of Refsum's disease, Abetalipoproteinemia, Tangier disease and Dejerine-Sottas syndrome.

2. The method of claim 1 wherein the peripheral demyelinating disease is hereditary.

3. The method of claim 1 wherein the inhibitor of VDAC1 activity is olesoxime.

4. The method of claim 1 wherein the inhibitor of VDAC1 expression is a siRNA.

5. The method of claim 1 wherein the inhibitor of VDAC1 activity is a small organic molecule.

* * * * *